US008043810B2

(12) United States Patent
Reif et al.

(10) Patent No.: US 8,043,810 B2
(45) Date of Patent: Oct. 25, 2011

(54) ANALYTE DETECTION USING AUTOCATALYTIC CHAIN REACTIONS

(75) Inventors: John H. Reif, Durham, NC (US); Peng Yin, Pasadena, CA (US); Thomas H. Labean, Hillsborough, NC (US); Geetha Shetty, Cary, NC (US); Erik A. Schultes, Durham, NC (US)

(73) Assignee: Eagle Eye Research, Inc., Durham, NC (US)

( * ) Notice: Subject to any disclaimer, the term of this patent is extended or adjusted under 35 U.S.C. 154(b) by 196 days.

(21) Appl. No.: 11/775,740

(22) Filed: Jul. 10, 2007

(65) Prior Publication Data

US 2009/0087838 A1    Apr. 2, 2009

Related U.S. Application Data

(60) Provisional application No. 60/915,659, filed on May 2, 2007.

(51) Int. Cl.
*C12Q 1/68* (2006.01)
*C07H 21/04* (2006.01)

(52) U.S. Cl. ...... 435/6.1; 435/6.11; 536/24.3; 536/24.33

(58) Field of Classification Search .................. None
See application file for complete search history.

(56) References Cited

U.S. PATENT DOCUMENTS

| 5,118,801 | A | 6/1992 | Lizardi et al. |
|---|---|---|---|
| 5,645,987 | A | 7/1997 | Richard |
| 5,714,320 | A | 2/1998 | Kool |
| 5,914,230 | A | 6/1999 | Liu et al. |
| 6,110,677 | A | 8/2000 | Western et al. |
| 2003/0065155 | A1* | 4/2003 | Usman et al. ............... 536/23.1 |
| 2005/0053962 | A1 | 3/2005 | Blackburn et al. |
| 2005/0227259 | A1 | 10/2005 | Zhang et al. |
| 2005/0260635 | A1 | 11/2005 | Dirks et al. |
| 2006/0035270 | A1 | 2/2006 | Lee et al. |
| 2006/0078910 | A1 | 4/2006 | Seeman et al. |
| 2006/0228733 | A1 | 10/2006 | Pierce et al. |
| 2006/0234261 | A1 | 10/2006 | Pierce et al. |
| 2006/0292561 | A1 | 12/2006 | Li et al. |
| 2007/0231810 | A1* | 10/2007 | Todd et al. ........................ 435/6 |

OTHER PUBLICATIONS

Heid et al., "Real time quantitative PCR," Genome Research, 1996, vol. 6, pp. 986-994.*
International Search Report and Written Opinion for PCT/US08/62579, mailed Feb. 10, 2009, 7 pages.
Levy et al., PNAS USA (2003) 100:6416-6421.

* cited by examiner

*Primary Examiner* — Young J Kim
(74) *Attorney, Agent, or Firm* — Morrison & Foerster, LLP; Kate H. Murashige

(57) ABSTRACT

Compositions and methods for detecting the presence of analytes employing autocatalytic chain reactions (ACR) having super linear kinetics for amplification of signal are disclosed.

9 Claims, 12 Drawing Sheets

8

ANALYTE DETECTION USING AUTOCATALYTIC CHAIN REACTIONS

CROSS-REFERENCE TO RELATED APPLICATION

This application claims priority from U.S. provisional application 60/915,659 filed 2 May 2007. The contents of this document are incorporated herein by reference.

STATEMENT OF RIGHTS TO INVENTIONS MADE UNDER FEDERALLY SPONSORED RESEARCH

This work was supported in part by a government contract: AFSOR SBIR Phase II contract FA8750-05-C-0062 entitled "A DNA Taggant Watermarking System." The U.S. government has certain rights in this invention.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2 (a)(C), is incorporated herein by reference in its entirety for all purposes. The sequence listing is identified on the electronically filed text file as follows:

| File Name | Date of Creation | Size (bytes) |
|---|---|---|
| 616322000100Seqlist.txt | Oct. 22, 2008 | 24,948 bytes |

TECHNICAL FIELD

The invention relates to analysis of small amounts of analyte in user-friendly formats that permit detection without special equipment. More particularly, the invention concerns assays that amplify a signal from an analyte to provide a detectable response.

BACKGROUND ART

Early approaches to chemical detection of analytes relied on chemical indicators to produce color changes or precipitation products giving readouts that are visible to the naked eye. These tests were therefore convenient, portable and economical, but relatively insensitive. More recently, the limits of detection have been dramatically lowered, both by the development of methods of separation to purify and concentrate the analyte and by the development of increasingly sophisticated instrumentation to detect analytes with greater specificity. However, both of these approaches require specialized equipment and skilled personnel to operate and are generally inapplicable to field testing.

There are many instances, such as in environmental studies, biomedical research and medical diagnosis, where there is a need for detection technology that can rapidly detect very low amounts of analytes as well as reduce the time for sample preparation, laboratory infrastructure and turnaround. For example, in localities where harsh socioeconomic conditions persist, diagnosis of infectious diseases would be benefited by techniques that are adaptable outside of conventional clinical laboratories. In addition, many military and commercial settings require the tracking of materials and/or documents and certification of their origin and authenticity. Tracking of materials or personnel may be accomplished by using a substance acting as a tag that is invisible until detected using specified analytical techniques. Presently, the methods of detecting such taggants are costly, laboratory-based and time-consuming.

The present invention provides assay compositions and methods that are adaptable to field use, simple to carry out, and able to detect very small amounts of analyte. The invention relies on amplification of a signal provided by the analyte by permitting the analyte directly or indirectly to trigger an autocatalytic chain reaction that amplifies the signal to produce products that are detectable by the naked eye.

Others have attempted to employ autocatalytic chain reactions (ACR's) to amplify analyte signals. For example, Dirks, et al., U.S. 2005/0260635 describe a method whereby metastable nucleic acid monomers can be made to self-assemble upon exposure to an analyte, thus obtaining a linear duplex polymer that can be detected by gel electrophoresis. No suggestion of a visible signal, such as color or fluorescence, is disclosed. Detection by fluorescence is, however, disclosed in Pierce, et al., U.S. 2006/0228733, a published application by the same group that employs a similar method of polymerization by an initiating oligonucleotide analyte. Similarly, in another publication of the same group, Pierce, et al., U.S. 2006/0234261, nanogold particles are used to detect the self-assembled polymers.

Zhang, et al., U.S. 2005/0227259 describe generation of an amplified signal indicative of a target nucleic acid molecule using detection by fluorescent resonance emission transfer (FRET) effected by a complex system of displacing looped nucleic acids that are bound to a fluorescence emitter and a quencher to produce a fluorescent signal.

Richard, U.S. Pat. No. 5,645,987 describes an isothermal polymerization reaction which may be used to amplify the signal generated by a catalytic primer substrate and the products are detected by various methods. Western, et al., U.S. Pat. No. 6,110,677 describe a different method of amplifying an initial oligonucleotide target for use in diagnostic methods. Seeman, et al., U.S. 2006/0078910 describe formations of nucleic acid nanostructures from crossover domains.

Levy, M., et al., *Proc. Natl. Acad. Sci. USA* (2003) 100: 6416-6421 describe a cross-catalytic cleavage method of amplification, but does not suggest its incorporation into assay methods. Lizardi, et al., U.S. Pat. No. 5,118,801 describe a signal amplification method which involves taking advantage of allosteric changes and employs conventional amplification methods and conventional detection using fluorescence and calorimetric methods. Liu, et al., U.S. Pat. No. 5,914,230 describe an alternative method of amplifying an initial nucleic acid signal and detection by means of a label.

Kool, U.S. Pat. No. 5,714,320 describes rolling circular amplification which is used in the present invention to generate signal amplification polymers.

The present invention provides particularly effective assay approaches which result in amplified signals permitting small amounts of analyte to be detected using convenient readouts requiring no instrumentation.

DISCLOSURE OF THE INVENTION

The present invention provides unique combinations of components of a sensitive detection system wherein the components comprise a nanoswitch detector (NSD) that triggers an autocatalytic chain reaction (ACR) that results in an amplification of signal by providing products that can be detected by an indicating detection reaction (IDR) that, if desired, can be designed to be detectable by the naked eye. In some cases, the analyte is, itself, the NSD. The autocatalytic chain reaction of the invention proceeds by superlinear kinetics to provide a plethora of product as compared to the amount of analyte present. Thus, the product will be present in much greater quantity than the original analyte. The IDR is designed to respond to product.

Thus, in one aspect, the invention is directed to a method to determine the presence or absence of an analyte in a sample. The sample is contacted with a reaction mixture which contains the NSD if needed, the components of the ACR, and the components of an IDR. If desired, the IDR may be added after the ACR is allowed to proceed. The analyte causes the NSD to trigger the ACR resulting in a multiplicity of product molecules that can be detected by the IDR.

When present, the NSD both targets the analyte and triggers the ACR. These functions can be included in separate molecules or in separate portions of the same molecule. In some embodiments, the NSD may include an allosterically responsive component that exposes or liberates a trigger, typically a nucleic acid, when bound to target analyte. This embodiment expands the scope of analytes that are candidates for testing by permitting interaction of molecules other than nucleic acids to effect the allosteric response, liberating a nucleic acid trigger.

The ACR may be an autocatalytic nucleic acid cleavage reaction, a hybridization chain reaction that exhibits superlinear kinetics, or a modified rolling circle amplification reaction that generates a multiplicity of IDR-reacting products, or may employ displacement of multiple fluorescent resonance emission transfer (FRET) pairs.

The invention further relates to reaction mixture compositions that comprise NSD, ACR and IDR components as well as to kits for constructing such reaction mixtures.

MODES OF CARRYING OUT THE INVENTION

Figure 1:
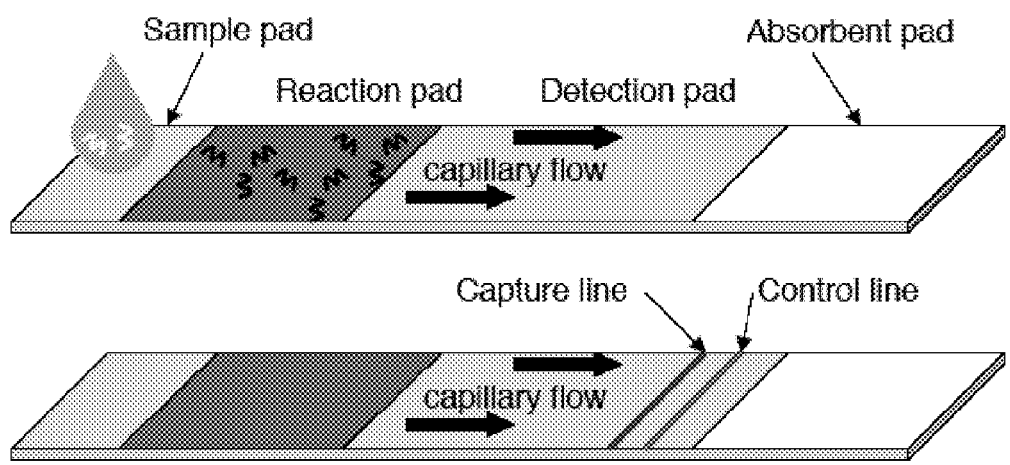
FIG. 1 illustrates a typical DNA detection assay in lateral flow strip format. Top panel: the liquid sample is applied on the left and flows through the reaction pad to the detection pad on the way to the absorbent pad on the right. Lower panel: the appearance of both a control line and a capture line indicate that the assay has been executed properly and that DNA was present in the sample.

By providing a nanoswitch detector (NSD) if needed, an autocatalytic chain reaction (ACR) that has at least superlinear or exponential kinetics, and components of an indicator detection reaction (IDR) that is responsive to the products of the ACR, detection of small amounts of analyte (even in complex mixtures) is made possible without resort to expensive instrumentation. Typically, the analyte is a nucleic acid, but the availability of allosteric and modular NSD systems allows translation of the signal received by interaction with any analyte into a trigger for the ACR. Allosteric systems which liberate nucleic acid triggers are known in the art and are described, for example, by Breaker, R. R., *Current Opinion in Biotechnol.* (2002) 13:31-39; by Ward, et al., U.S. 2006/0035275; and by Nilsen-Hamilton, U.S. 2005/0026178. In these embodiments, a conformational change in a molecule that changes its shape in response to peptides, small molecules, energy packets, and the like, is induced to release or expose a nucleic acid trigger for the ACR. "Energy packets" refers to photons or emissions from radioactive substances (including α and β particles, for example), that activate any of a large class of photosensitizers, such as those mentioned in U.S. Pat. No. 6,723,750.

There are various methods of sequestering nucleic acid sequence(s) that trigger the ACR. One method, strand displacement via 'toe-hold' mediated branch migration, has a well established prior art. In strand displacement, the trigger sequence is bound in a metastable duplex configuration with either an intermolecular or an intramolecular complementary sequestering strand, which blocks the trigger from activating the ACR. The sequestering strand is composed of sequence and/or structural features that make it susceptible to displacement from the trigger by the more stably binding analyte. In the presence of the analyte, which is frequently, but not necessarily, another single-stranded nucleic acid, the sequestering strand is efficiently displaced (typically as a duplex with the analyte), to liberate the trigger stand to initiate the ACR.

Another method of sequestering nucleic acid sequence(s) that act as triggers of the ACR, is based on a conformational response to the analyte interaction with the NSD at a site other than the sequestered trigger sequence. Upon interacting with the analyte, the NSD undergoes a conformational shift that liberates or exposes the trigger sequence for subsequent activation of the ACR. As noted above, allosteric modulation of the NSD has the advantage that the analyte need not be a nucleic sequence, but may belong to virtually any type of molecule, for example, small organic and inorganic species, environmental contaminants, and biological molecules, such as peptides and proteins, carbohydrates and lipids. The analyte could include various forms of energy, as long as the energy is capable of inducing the allosteric transformation liberating the sequestered trigger strand. Photosensitive NSD's or NSD's sensitive to the ionizing radiation of radioisotopes could be used as detectors of radioactive contamination. Nucleic acids responding to analytes in this way have been isolated from nature and synthesized in vitro, as described in U.S. 2005/0026178 and U.S. 2006/0035275 cited above.

A strand displacement and allosteric modulation system using riboswitches can also be used to implement the NSD. Absent the analyte, the triggering strand of the NSD is sequestered, preempting activation of the ACR. In the presence of the analyte, the allozyme undergoes a conformational switch, exposing the triggering strand, and initiating the ACR.

In some embodiments, the portion of the NSD that interacts directly with the analyte, and the triggering oligonucleotide are separate components. For example, the analyte effects a conformational change in a first component which exposes a nucleic acid sequence that activates the trigger for the ACR. Typically, an analyte nucleic acid opens a loop sequence in a component of the NSD which in turn opens and exposes the trigger for the ACR.

In another embodiment, the NSD is a circular, especially designed single-stranded nucleic acid that serves as a template for rolling circle amplification as described by Kool in U.S. Pat. No. 5,714,320, cited above. In this embodiment, the circular DNA is designed to include at least one restriction site which, in the presence of restriction enzyme, permits cleavage of the extended DNA strand when coupled to added snippets of DNA that complement the restriction site. The multiplicity of fragments generated by the single-strand upon cleavage permits easy detection by virtue of the presence of a multiplicity of such segments. Such fragments can prime amplification on additional circles, thus providing superlinear production of fragments for detection.

In still another embodiment, the analyte itself in effect behaves as a trigger by liberating multiple detectable complements that are bound to a single-chain DNA of repeating sequences generated, for example, by the rolling circle amplification method.

The ACR in the methods of the invention may take several forms. In one embodiment, a cross-catalytic nucleic acid cleavage ACR is employed. The NSD trigger causes linearization of a ribozyme contained in a reaction mixture of complementary circularized forms of the ribozyme. The linearized trigger cleaves the circularized form of its complementary embodiment, which then becomes active and cleaves and linearizes the circularized form of its complement; each open linearized form is then able to cleave the circularized form of its complement, resulting in a cross-cleavage catalytic reaction with superlinear kinetics.

In this embodiment, the reaction mixture for conducting the method of the invention will contain, as a component of the NSD, a form of the ribozyme that is activated directly or indirectly by the analyte, as further described in Example 1, as well as multiple copies of circularized complementary forms of the ribozyme. The product comprises the linear forms of the complementary ribozyme constructs. The amount of product is limited only by the concentration of circularized ribozyme present in the reaction mixture.

Figure 3:
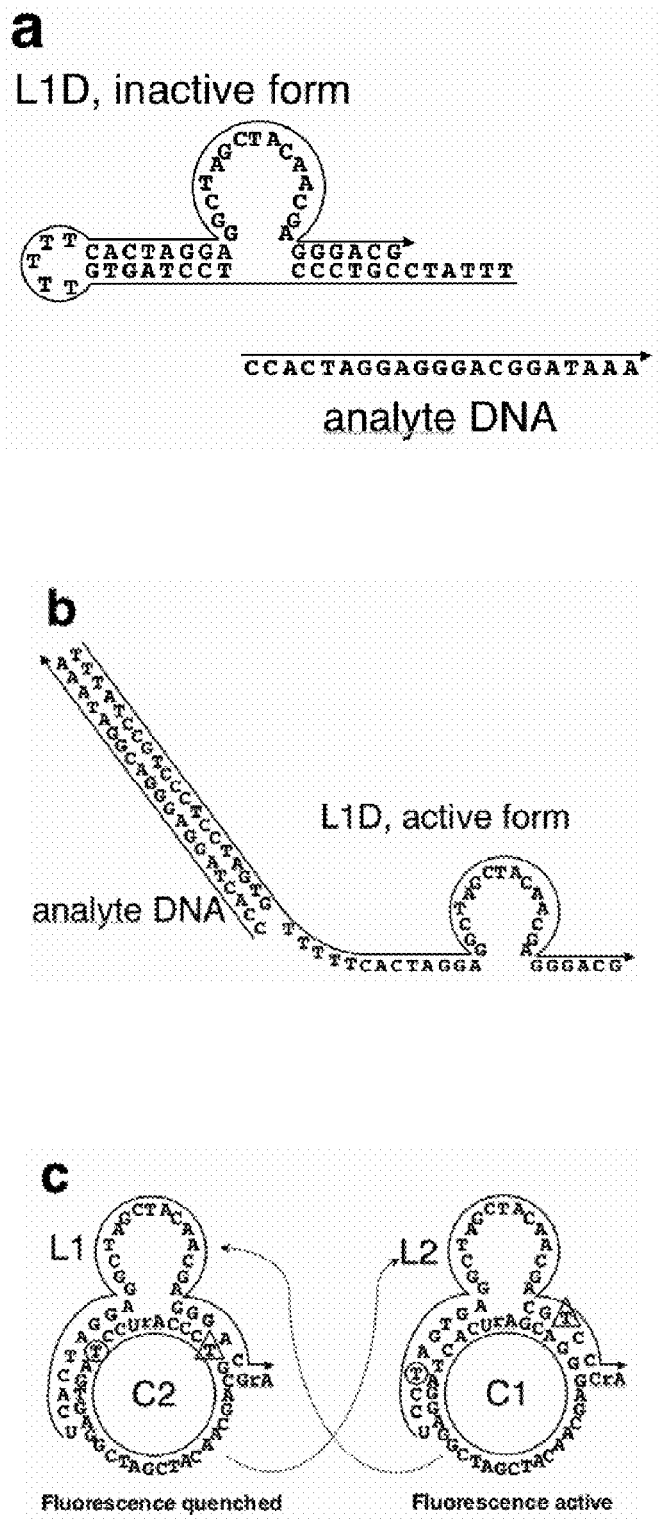
FIGS. 3a-3c show schematics of a FRET based IDR (SEQ ID NOS:1-4).

The linearized forms of the circular ribozymes can be detected by a variety of methods. For example, the sequences proximal to either side of the cleavage site may each contain a member of a FRET pair. Alternatively, the linearized forms of the ribozyme may be used to bridge metal colloids, such as gold nanoparticles, that have been derivatized with oligomers complementary to portions of the linearized sequences. For instance, when diffused in solution, gold nanoparticles appear red, but when brought into close proximity they appear blue due to plasmon resonance. These alternatives are illustrated below in Examples 1.1 and 1.2 and in FIGS. 3 and 4. These examples are used only for illustration, and any method that distinguishes the linear forms of the ribozymes from the circular forms could be used. For example, a fluorescent dye coupled to a complementary oligomer which binds only to the linearized form could be used for detection.

In another embodiment, the hybridization chain reaction described by Dirks, R. M., et al., in *Proc. Natl. Acad. Sci. USA* (2004) 43:15275-15278 may be modified to exhibit superlinear kinetics, rather than the linear kinetics characteristic of the reaction as described in the art. The components of the reaction mixture in this case are a pair of at least double-looped structures wherein opening both loops of the structure of one of these components provides binding sites for two molecules of the other component. Superlinear kinetics result because opening of one of these double-loop structures by interaction with analyte provides binding for two molecules of the other component, which, when opened, provide binding sites for four molecules of the first component, which results in opening of these components' structures to provide eight binding sites on the next level. The resultant is a dendritic structure containing members of both components that can be readily detected by labeling its extended positions with complementary oligomer-bound label. In the exemplified embodiment, colloidal gold nanoparticles are used as the label.

In this case, the amount of dendritic structures formed is limited only by the amounts of reciprocally interacting and hybridizing components contained in the reaction mixture. Again, alternative methods of detection may be used other than colloidal metals, including binding to radioisotopes, fluorophores or other labels. In this embodiment, the NSD is the analyte itself which initiates the ACR by opening one of the components for the reciprocal hybridization chain reaction.

In still another embodiment, the reaction mixture contains a circular single-stranded DNA comprising at least one sequence complementary to analyte and one or more restriction sites separating the remaining sequences. A processive polymerase present in the reaction mixture catalyzes rolling circle amplification when the reaction is primed by the analyte, complementary to one of the sequences in the circular DNA. The continued amplification of the sequence in the circle generates a series of repeating sequences in the single-stranded product separated by restriction sites which are made susceptible to cleavage by short complements to their sequences also contained in the reaction mixture. Upon cleavage of the generated single-strand, a multiplicity of single-stranded sequences is generated which can be used to effect the assembly of metal colloids into a complex resulting in a change in color. Furthermore, some of the single-stranded products have sequences identical to the analyte DNA, and can thus prime additional circular DNA templates, ensuring a superlinear amplification of product for both detection (assembly of nanoparticles) and amplification (via priming). Thus, the gold particles are coupled to oligomers with sequences complementary to the generated single-strand segments such that the gold particles are assembled into a multi-particle complex.

In this embodiment, the reaction mixture will contain the circular DNA, the appropriate polymerase, short DNA molecules complementary to the restriction sites, the appropriate restriction enzyme, nucleotides for assembly of the single-strand, and, during the reaction or afterwards, the detecting gold particles associated with complementary oligomers.

In still another embodiment of the invention, rolling circle amplification (or any other method) can be used to assemble a single-chain DNA with repeating sequences wherein in each sequence, there is a binding site for analyte and a binding site for a FRET detector. In preparation for the assay, the single strand is coupled to a multiplicity of FRET detectors, i.e., oligomers, each containing a fluorescent emitter and quencher, wherein the oligomers are constrained by binding to the single strand to permit quenching to occur. Addition of the analyte in the presence of a processing polymerase permits ongoing construction of the complementary strand, thus displacing the multiplicity of FRET detectors and allowing detection of fluorescence generated thereby. Alternatively, the single-chain could be assembled synthetically containing only one or two sites of attachment for the analyte and a multiplicity of sites to attach the FRET detector sequences.

The assays of the invention can also be configured in single-use disposable lateral flow strips for field use. Lateral flow assays were developed in the late 80's drawing on technology disclosed in Campbell, R. L., et al. (U.S. Pat. No. 4,703,017) and Rosenstein, et al. (U.S. Pat. No. 4,855,240). Today they are used routinely for home pregnancy tests, human fecal occult blood detection, HIV-1 diagnostics, mycobacterium tuberculosis diagnostics, and detection of drugs of abuse, for example. The lateral flow assay format is simple to use and can be read with the naked eye.

The lateral flow format consists of a plastic-backed strip with sample application area on one end and an absorbent pad on the other end, which causes the sample to be drawn through the reaction area and detection pads by the absorbent action of the terminal pad. DNA molecules in the sample are exposed to reagents in the proper order by patterning them in sequence on the various pads during the manufacturing process. FIG. 1 illustrates a typical DNA detection assay in lateral flow strip format.

A lateral strip of nitrocellulose incorporates the reagents of the NSD, ACR and IDR. Assays configured with a lateral flow IDR format should yield results within 5-10 minutes. Tests strips should be stable for at least several months and perhaps up to a year, making this incarnation ideal for portable and inexpensive kits for field-based detection and diagnosis.

In the examples set forth below, particular illustrations of the assay are given with particular embodiments of the NSD, ACR and IDR in each case. In some examples, the analyte itself is the NSD. However, in each case, it is possible to modify the assay so that an intermediate will release a trigger in the presence of an analyte. Thus, instead of utilizing the analyte itself as the NSD in Example 5, the analyte could be used to release the primer for the polymerase. Typically, for example, an allosteric molecule sequestering the primer might interact with an analyte of any arbitrary nature to release the primer. Similarly, IDR components are generally interchangeable among the assays.

The following examples are offered to illustrate but not to limit the invention. In the descriptions, asterisks are used to indicate complementary sequences—i.e., a* indicates a sequence complementary to a, b* indicates a sequence complementary to b. Alternatively, the notation $\bar{a}$ indicates a sequence complementary to a and $\bar{b}$ indicates a sequence complementary to b. Sequences are listed in 5'→3' order, or when diagrammed an arrow (→) indicates the 5'→3' sequence.

EXAMPLE 1

Cross Catalytic Cleavage ACR

In this example, the autocatalytic chain reaction (ACR) is an exponential cross-catalytic cleavage reaction catalyzed by the 10-23 deoxyribozyme as described in Levy, M., et al., *PNAS* (2003) 100:6416, incorporated herein by reference. The 10-23 deoxyribozyme is a highly efficient and sequence specific enzyme for cleaving RNA or ribonucleic acid phosphodiester linkages within DNA sequences. The 10-23 deoxyribozyme does not cleave DNA linkages. A circular form of this enzyme is inactive, but the linear form is catalytic.

Figure 2:
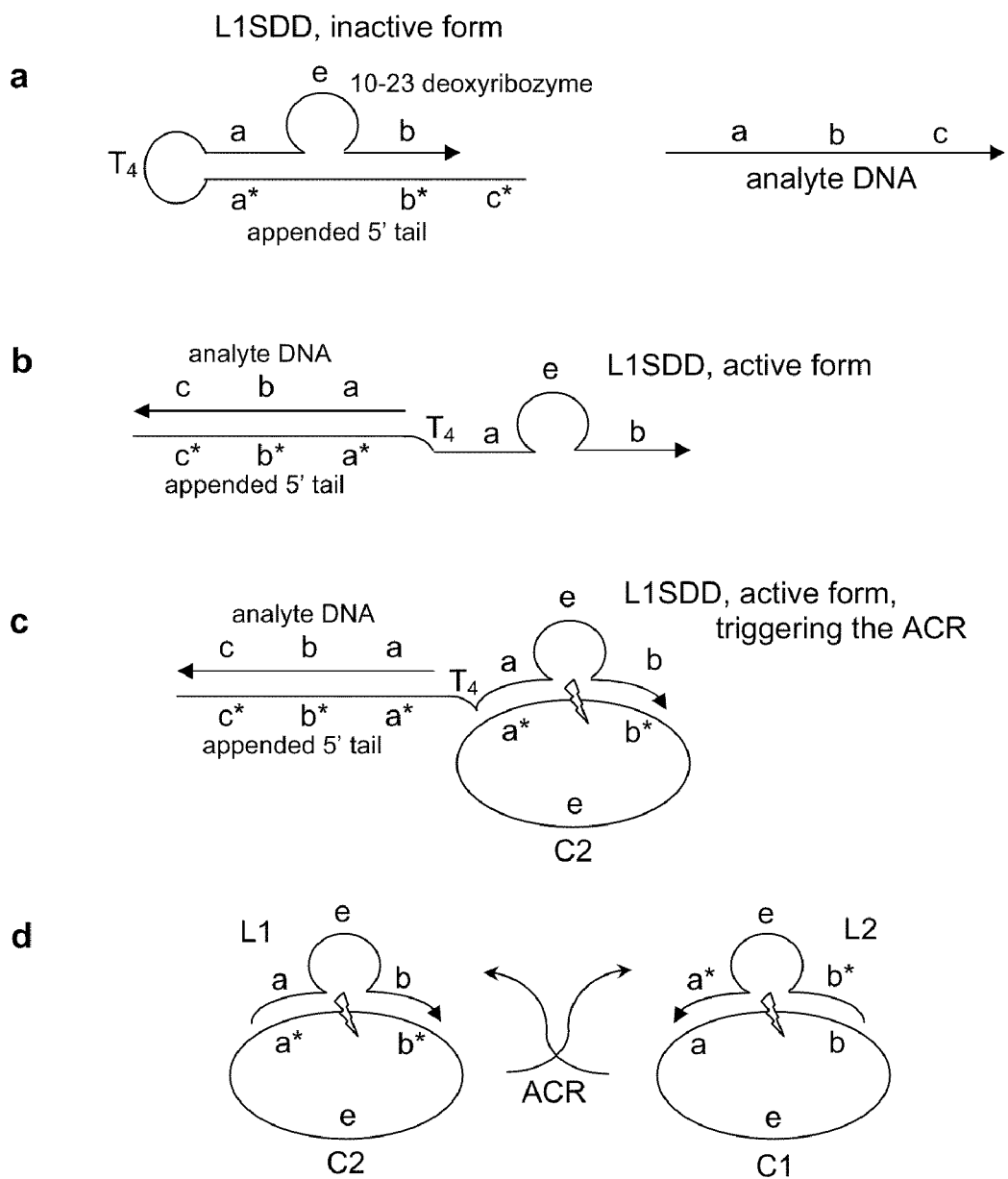
FIGS. 2a-2d show an overview of the deoxyribozymogen NSD/ACR method.

The ACR employs a mixture of circularized, hence inactivated, 10-23 deoxyribozymes, C1 and C2, each containing a small RNA portion susceptible to cleavage. See FIG. 2. C2 can hybridize with, and can subsequently be cleaved by, a cleaved and linearized C1 (designated L1). Symmetrically, C1 can be cleaved by an active L2, which is a linearized C2. The products of the activated ACR, L1 and L2, thus accumulate exponentially.

In one embodiment, the nanometer scale switching device (NSD) is itself a 10-23 deoxyribozyme that has been modified to be activated by an analyte. This modified 10-23 deoxyribozyme is generically referred to as L1D (Loop 1 Detector). Absent the analyte, the L1D is in an inactive state. When contacted by the analyte, L1D is activated and acts as a trigger initiating the ACR.

The accumulation ACR products, L1 and L2 may be detected by a variety of methods.

EXAMPLE 1.01

In this incarnation, the NSD is a 10-23 deoxyribozyme which has been modified for strand displacement using a 5' appended, 21 nucleotide tail. See FIG. 2a, where it is labeled as L1SDD (Loop 1 Strand Displacement Detector). L1SDD has substrate recognition sub-sequences, a and b, the enzyme sub-sequence e, and the 21 nucleotide tail tethered by a tetraloop, $T_4$ (TTTT). The 21 nucleotide tail has a sequence that is complementary to the 10-23 deoxyribozyme substrate recognition sub-sequences (a*b*) plus an additional 5' sequence, c*, that facilitates analyte hybridization. The analyte DNA has the sequence (from 5' to 3') a b c.

Absent the analyte, L1SDD has a hairpin structure that inactivates the deoxyribozyme. When contacted by the analyte, the tail and analyte hybridize, opening the hairpin to its open active configuration, see FIG. 2b. In the analyte-bound open form, L1SDD acts as a trigger initiating the ACR as described above, see FIG. 2c.

In FIGS. 2A-2d, arrowheads indicate 3' end of DNA oligomers. Asterisks designate the reverse complement of cognate sequence pairs. The lightning icon indicates catalyzed cleavage of circularized DNA. FIG. 2a shows the NSD L1SDD in its inactive form. Sub-sequence c of the analyte DNA facilitates its hybridization to sub-sequence c* of L1SDD's 5' appended tail. FIG. 2b shows L1SDD in its activated form, after the appended tail hybridizes to the analyte DNA. FIG. 2c shows the activated L1SDD acts as a trigger, initiating the ACR by catalyzing the opening of a circularized 10-23 deoxyribozyme, C2. FIG. 2d shows the cross-catalytic exponential amplification of circularized DNA openings results in an accumulation of L1 and L2 as products.

EXAMPLE 1.02

This incarnation is similar to Example 1.01, except the NSD is a circularized 10-23 deoxyribozyme as in construct C1 that has been hybridized to a texaphyrin-oligonucleotide conjugate. The texaphyrin-oligonucleotide conjugate can photo-induce sequence-specific cleavage of C1 when the appropriate photon energy is present. The photo-cleaved, open form of C1 acts, in a manner analogous to Example 1.01, as a trigger for ACR. This construct is therefore a sensitive detector for specific photon energies (in this case, low-energy radiation between 690-880 nm). This C1-texaphyrin-oligonucleotide complex NSD is referred to as L1hvD1 (Loop 1 Photon Detector 1).

Neither the electromagnetic radiation nor the texaphyrin-oligonucleotide conjugate alone will induce cleavage. Absent the photon analyte, the closed-circle configuration of L1hvD inactivates the deoxyribozyme and the ACR remains in its poised state. Photosensitizer-oligonucleotide conjugates having absorbencies in other energies, acting either independently or multiplexed, could be used as sensitive detectors of radioisotope contamination.

EXAMPLE 1.03

This incarnation is similar to Example 1.02, except the circularized 10-23 deoxyribozyme is linked directly to a texaphyrin photosensitizer, without an intermediary oligonucleotide conjugate. The texaphyrin link can directly photoinduce sequence specific cleavage of C1 when the appropriate photon energy is present. This C1 texaphyrin linked NSD is referred to as L1hvD2 (Loop 1 Photon Detector 2). Photosensitizer oligonucleotide conjugates having absorbencies in other energies, acting either independently or multiplexed, could be used as sensitive detectors of radioisotope contamination.

EXAMPLE 1.04

This incarnation is similar to Example 1.01, except the NSD is a modified 10-23 deoxyribozyme which has been conjugated or concatenated to a nucleic acid aptamer or enzyme capable of allosteric modulation, as described in U.S. 2005/0026178 and U.S. 2006/0035275A1, wherein the molecule referred to therein as the "allosteric effector" is the analyte. This particular NSD construct is referred to as L1AD (Loop 1 Allozyme Detector).

Allozyme-based NSD's are capable of detecting a wide range of analytes, from small molecule (including divalent metal ions) to macromolecular structures. Absent the allosteric effector-analyte, the conformation of L1AD inactivates the deoxyribozyme. In the presence of the analyte, the allozyme undergoes an conformational switch, activating the 10-23 deoxyribozyme.

EXAMPLE 1.1

Use of FRET as IDR

This example is shown in FIGS. 3a-3c. In FIG. 3a, the NSD and analyte are depicted with particular sequences. FIG. 3b shows the analyte DNA binding L1D, activating the 10-23 deoxyribozyme. FIG. 3c depicts the quenched (C2) and fluorescing (L2) FRET pairs (circled T and triangle encased T) where L2 is shown hybridized to C1.

L1D is 5'-TTT ATC CGT CCC TCC TAG TGT TTT TCA CTA GGA GGC TAG CTA CAA CGA GGG ACG (SEQ ID NO:1), and the analyte DNA sequence is 5'-CCA CTA GGA GGG ACG GAT AAA (SEQ ID NO:2). The C1 and C2 constructs are prepared by enzymatically circularizing appropriate linear DNA constructs with CircLigase™, obtained from Epicenter Biotechnologies. The linear forms of C2 and C1 are respectively: 5'-p-AGC TAC AAC GAC GTC CCrA UCC TAG TGA GGC T (SEQ ID NO:3) and 5'-p-AGC TAC AAC GAG GGA CGrA UCA CTA GGA GGC T (SEQ ID NO:4). The linear C1 and C2 sequences contain, at the appropriate positions, a single ribo-linkage (depicted in the figures as "r") in the otherwise deoxy-chain, that serve as substrates for the deoxyribozyme cleavage reaction in the linearization of circles as part of the ACR.

For detection using fluorescence resonance energy transfer (FRET), the donor dye FAM and an acceptor dye TAMRA are respectively attached to the circled T and the triangle-encased T in strand C2. In C2, FAM and TAMRA are positioned in close proximity, allowing strong FRET between the two. In contrast, after linearization (i.e., the formation of L2), the distance between the two dyes is increased, inhibiting FRET, so the accumulation of strand L2 can be detected by monitoring an increase in fluorescence.

A system that contains 2 µM C1, 2 µM C2, and 0.1 µM L1D, can readily detect presence of 0.1 µM analyte DNA.

EXAMPLE 1.2

Use of Gold Nanoparticles as IDR

Alternatively, detection of the products formed in the ACR of Example 1.1 is based on colloidal solution of gold-nanoparticles (AuNP's). When dispersed, AuNP's appear red, when aggregated, such that the particles experience plasmonic coupling, the AuNP's appear blue. AuNP's are functionalized with thiolated single-stranded DNA oligomers, and particle aggregation is specifically induced where sequence hybridization binds particles in close proximity. See U.S. 2006/0234261, Elghanian, R., et al., *Science* (1997) 277:1078, and Storhoff, J. J., et al., *J. Am. Chem. Soc.* (1998) 120:1959. AuNP aggregation can be induced between particles functionalized with complementary DNA sequences, or through the use of DNA oligomers that can bridge the sequences functionalized to the particles.

Figure 4:
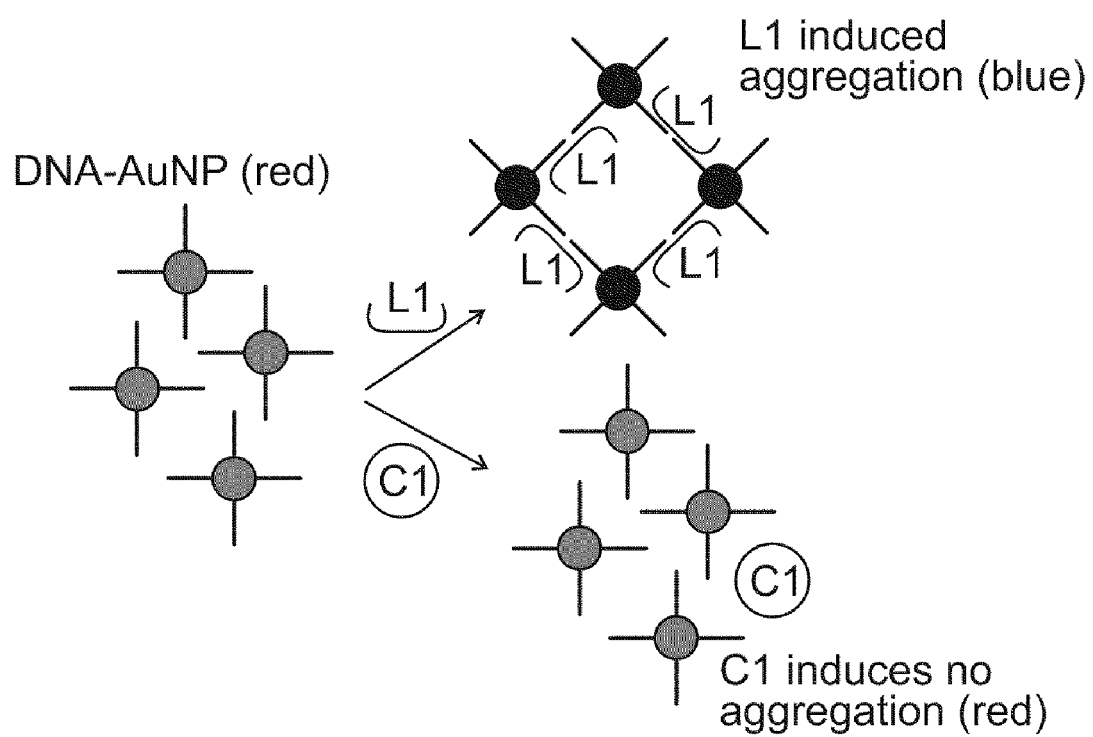
FIG. 4 shows an example of DNA-functionalized gold nanoparticle (DNA AuNP) colorimetric IDR.

The present embodiment is schematically depicted in FIG. 4. In the presence of the analyte DNA and subsequent triggering of the ACR, the accumulated product of the ACR, L1 acts as a bridge, aggregating AuNP's, inducing plasmonic coupling and the red to blue color change. Although the DNA strands of the DNA-AuNP are also complementary in sequence to strands C1, L1 more effectively bridges dispersed AuNP's. The relative inability of C1 to serve as the bridging strand is attributed to steric hindrance. The reaction proceeds most efficiently if the DNA-AuNP is added after the ACR reaction has run for 2 hours.

In one illustrative procedure, 15 nm (standard deviation ±40 nm) diameter AuNP's (Ted Pella, Inc.) were functionalized with synthetic DNA oligomers having the sequences: 5'-GCT AGC CTC ACT AGG A-$A_{10}$-C6 SS (SEQ ID NO:5) or 5'-C6 SS-$A_{10}$-TGG GAC GTC GTT GTA (SEQ ID NO:6).

The included $A_{10}$ sub-sequence facilitates accessibility of the oligos during hybridization. The C6SS "thiol modifier" is a 6-carbon-alkane-disulfide group capping the 5' ends of the synthetic oligomers, that promotes stable linkage of the DNA to the AuNP. The C6SS modifications were prepared as part of the synthesis of the DNA oligomers.

This procedure can also be performed in a solid matrix in a lateral flow format. A cellulose- or nylon-based membrane "paper" strip or "dip-stick" is charged with the necessary reagents to support the plasmonic colorimetric assay, obviating complex preparatory and disposal procedures, Liu, J., et al., *Angew. Chem. Int. Ed.* (2006) 45:7955, Corstjens, P., et al., *Clinical Chemistry* (2001) 47:1885, and U.S. Pat. Nos. 5,616,478, and 6,225,062.

A. The autocatalytic cross cleavage procedure using the detection method of this example is conducted to detect a genomic sequence uniquely identifying *Chlamydia trachomatis*, Girjes, A. A., et al., *Res. Microbiol* (1999) 150:483. The sequences used are:

L1D:
5'-CCG ACC TTT GGG TTA TGA GCC CAT TTT TGG GCT CAG

GCT AGC TAC AAC GAT AAC CCA (SEQ ID NO: 7);

analyte DNA:
5'-TGG GCT CAT AAC CCA AAG GTC GG (SEQ ID NO: 8);

Linear C2:
5'-p-AGC TAC AAC GAT GGG TTA rAUG AGC CCA GGC T (SEQ ID NO: 9);

Linear C1:
5'-p-AGC TAC AAC GAT AAC CCA rAUG GGC TCA GGC T (SEQ ID NO: 10);

C6SS capped DNA for AuNP functionalization:
5'-GCT AGC CTG GGC TCA-$A_{10}$-C6SS (SEQ ID NO: 11), and

5'-C6SS-$A_{10}$-TTA ACC CAT CGT TGT A (SEQ ID NO: 12).

B. The procedure of this example is conducted to detect a unique identifier of Human Immunodeficiency Virus (HIV), Cao, Y. C., et al. (supra). The sequences used are:

L1D:
5'-GTC ATG TTA TTC CAA ATA TCT TCT TTT GAA GAT AGG

CTA GCT ACA ACG ATT TGG AA;

analyte DNA:
5'-GAA GAT ATT TGG AAT AAC ATG AC;

Linear C2:
5'-p-AGC TAC AAC GAT TCC AAA rAUA TCT TCA GGC T;

Linear C1:
5'-p-AGC TAC AAC GAT TTG GAA rAUG AAG ATA GGC T;

C6SS capped DNA for AuNP functionalization:
5'-GCT AGC CTG AAG ATA-$A_{10}$-C6SS, and

5'-C6SS-$A_{10}$-TTT GGA AAT CGT TGT A.

C. The procedure of this example is conducted to detect an additional unique identifier of Human Immunodeficiency Virus (HIV), Cao, Y. C., et al., *Science* (2002) 297:1536. The sequences used are:

L1D:
5'-GCC AGG ACT CTT GCC TGG AGC TGC TTA ATG CCC CAG

ACC GTG AGT TTTT ACT CAC GGT CTG GGG CAG GCT AGC

TAC AAC GAT TAA GCA GCT CCA GGC (SEQ ID NO: 19);

analyte DNA:
5'-ACT CAC GGT CTG GGG CAT TAA GCA GCT CCA GGC AAG

AGT CCT GGC (SEQ ID NO: 20);

Linear C2:
5'-p-AGC TAC AAC GAC TGC TTA ArAU GCC CCA GAG GCT (SEQ ID NO: 21);

Linear C1:
5'-p-AGC TAC AAC GAT TAA GCA GrAU CTG GGG CAG GCT (SEQ ID NO: 22);

C6SS capped DNA for AuNP functionalization:

5'-GCT AGC CTG CCC CAG A-$A_{10}$-C6SS (SEQ ID NO: 23), and

5'-C6SS-$A_{10}$-TCT GCT TAA TCG TTG TA (SEQ ID NO: 24), or

5'-GCT AGC CTC TGG GGC A-$A_{10}$-C6SS, (SEQ ID NO: 25), and

5'-C6SS-$A_{10}$-TTT AAG CAG TCG TGG TA (SEQ ID NO: 26).

D. The procedure of this example is conducted to detect a longer form of a uniquely identifying genomic sequence from *Chlamydia trachomatis*, Girjes, A. A., et al. (supra). The sequences used are:

L1D:
5'-GGA TTC GGA CCT CCG ACC TTT GGG TTA TGA GCC CAA

CGA GAT TTT TAT CTC GTT GGG CTC AGG CTA GCT ACA

ACG ATA ACC CAA AGG TCG G (SEQ ID NO: 27);

analyte DNA:
5'-ATC TCG TTG GGC TCA TAA CCC AAA GGT CGG AGG TCC

GAA TCC (SEQ ID NO: 28);

Linear C2, Linear C1, and the C6SS capped DNA for AuNP functionalization are the same as in Example 1.2A.

Figure 5:
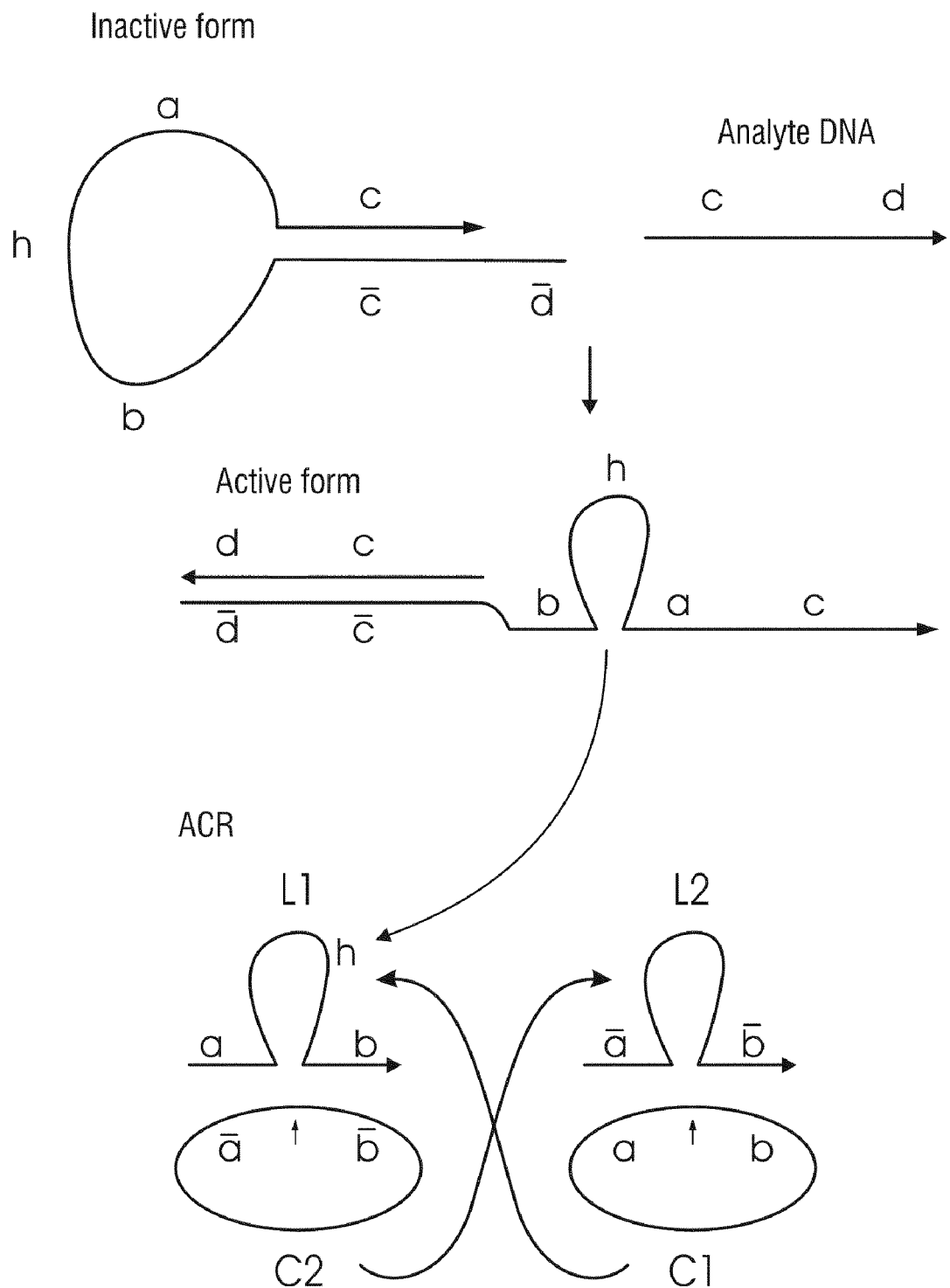
FIG. 5 shows an alternative configuration of the NSD used in autocatalytic cleavage ACR of FIGS. 2a-2d.

E. Detection of different or multiple analytes using the same NSD triggering mechanism, is permitted if the sequence of the 10-23 deoxyribozyme and its recognition sites are not a part of the sequence that hybridizes to the analyte DNA sequence. Thus, as shown in FIG. 5, the sites a-h-b recognition sites for the ribozymes are not a part of the analyte recognition sets a* or b*. The sequences used are:

L1D:
5'-ATC CAG GTC ATG TTA TTC CAA ATA TTT ATC CGT CCC

TCC TAG TGG TCA CTA GGA GGC TAG CTA CAA CGA GGG

ACG TAT TTG GAA TAA CAT (SEQ ID NO: 29);

analyte DNA:
5'-TAT TTG GAA TAA CAT GAC CTG GAT (SEQ ID NO: 30);

Linear C2:
5'-p-AGC TAC AAC GAC GTC CCrA UCC TAG TGA GGC T (SEQ ID NO: 31); and

Linear C1:
5'-p-AGC TAC AAC GAG GGA CGrAUCA CTA GGA GGC T (SEQ ID NO: 32).

EXAMPLE 1.3

Separation of NSD Function into Two Molecules

Figure 6:
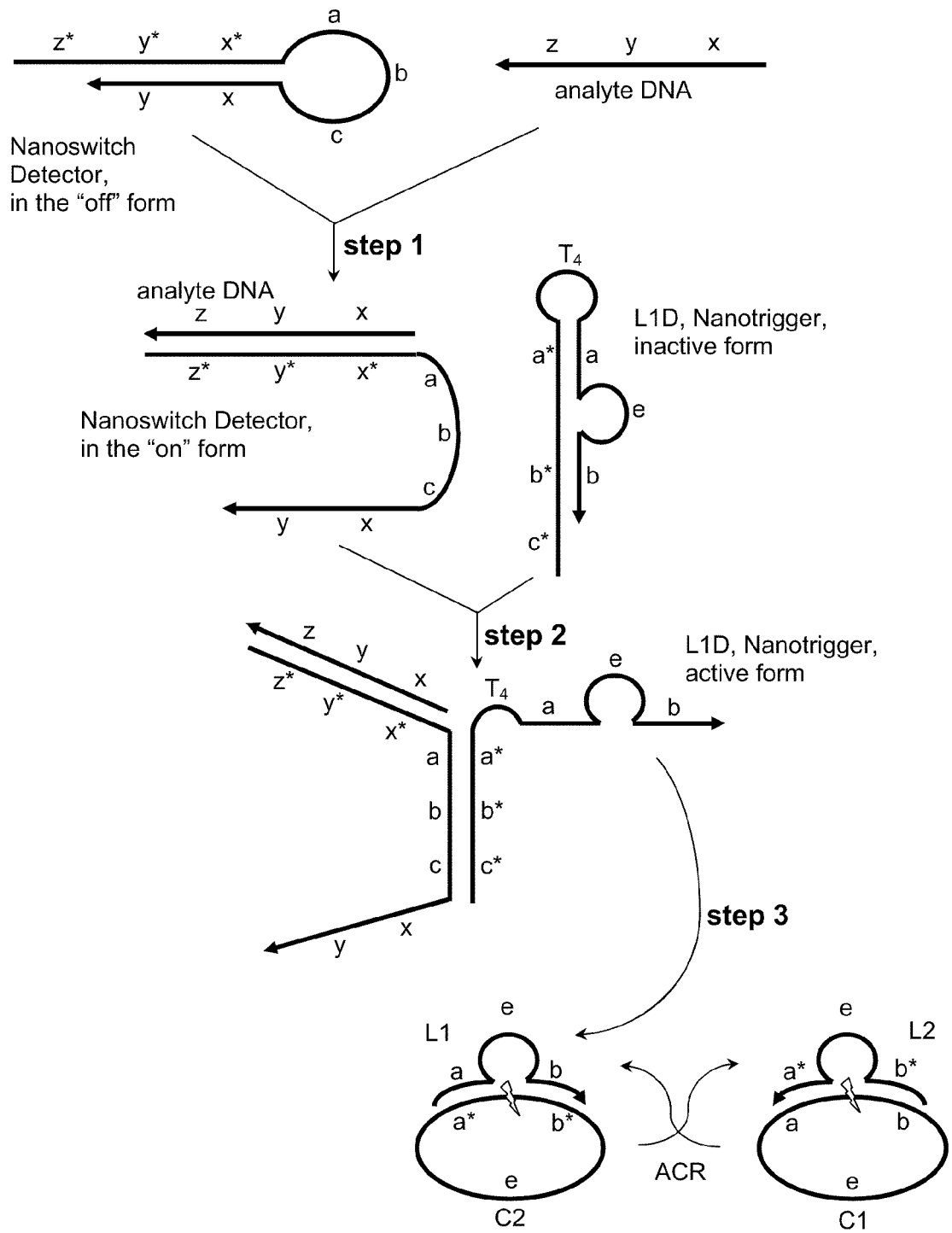
FIG. 6 shows another alternative configuration of the NSD used in the autocatalytic cleavage ACR of FIGS. 2a-2d.

Instead of a single NSD embodying both the analyte detection and triggering of the ACR, two distinct and independent nanostructures embodying each function separately are employed. (See FIG. 6.)

In Step 1, the Nanoswitch Detector is a hairpin that opens in the presence of the analyte DNA exposing sub-sequences a-b-c. In Step 2, the exposed a-b-c sub-sequence opens the a*-b*-c* stem of L1D. In Step 3, the activated form of L1D binds to C2, initiating the ACR.

Hence, in this incarnation, L1D performs only the triggering function of the NSD. This 2-step NSD module is designed to decrease false positives.

A. In one embodiment, this procedure is designed to detect a 40-nucleotide analyte DNA from the 7.4 kb multicopy cryptic plasmid of the *Chlamydia trachomatis* genome, 5'-CAA CAC CTG TCG CAG CCA AAA TGA CAG CTT CTG ATG GAA T (SEQ ID NO:33). This common plasmid is found in human biovar strains of *Chlamydia* (Palmer, L., et al., *Plasmid* (1986) 16:52-62; Little, M. C., et al., *Clinical Chemistry* (1999) 45:777-784).

Nanoswitch Detector is:

5'-ATT CCA TCA GAA GCT GTC ATT TTG GCT GCG ACA GGT GTT GCA CTA GGA GGG ACG GAT AAA CAA CAC CTG TCG CAG CCA AAA TGA C (SEQ ID NO: 34);

L1D is:
5'-TTT ATC CGT CCC TCC TAG TG TTTT CA CTA GGA GGC TAG CTA CAA CGA GGG ACG (SEQ ID NO: 35);

Linear C2, Linear C1, are the same as in Example 1.1, while the C6SS capped DNA for AuNP functionalization is the same as in Example 1.2.

B. In another embodiment of this example, a different *Chlamydia trachomatis* cryptic plasmid sequence, DNA (41 nucleotides), 5'-GTC GCA GCC AAA ATG ACA GCT TCT GAT GGA ATA TCT TTA AC (SEQ ID NO:36) is detected using this procedure wherein the Analyte Detector (86 nucleotides) is 5'-GTT AAA GAT ATT CCA TCA GAA GCT GTC ATT TTG GTG CGA CCA CTA GGA GGG ACG GAT AAA GTC GCA GCC AAA ATG ACA GCT TCT GA (SEQ ID NO:37).

C. In another embodiment, a shorter Analyte Detector sequence for the analyte of the previous paragraph (70 nucleotides), 5'-TTC CAT CAG AAG CTG TCA TTT TGG CTG CGA CCA CTA GGA GGG ACG GAT AAA GTC GCA GCC AAA AT GAC AG (SEQ ID NO:38) is used.

EXAMPLE 2.0

(HCR) with Super Linear Kinetics

In this example, the ACR is an improvement of the Hybridization Chain Reaction (HCR) described by Dirks, R. M., et al., *PNAS* (2004) 101:15275, and in U.S. 2005/0260635, U.S. 2006/0234261 and U.S. 2006/0228733. The HCR as described in these documents has linear kinetics, whereas the improved ACR described herein has super linear kinetics. In addition, the product of the HCR as described in the cited documents results in a linear double-stranded nanostructure complex, in contrast to the product of the present example which is a nanostructure complex that has dendritic characteristics. The dendrite structure facilitates detection and enhances sensitivity. The ACR in this embodiment is as outlined below and illustrated in FIGS. 7a-7f.

The process requires the presence of two hairpin-containing structures, each hairpin containing two looped segments. In the simplest embodiment the loops are of identical sequence. The sequence of the loops in one of the hairpin molecules is complementary to an extended single-stranded region of the other. The analyte target nucleic acid is able to open the entire hairpin of one of the molecules, permitting the opened structure to hybridize to two molecules of the second hairpin, thus opening two molecules of the second hairpin, which each in turn can hybridize and open two molecules of the first. This reciprocal opening and hybridization results in a tree-like structure.

Figure 7A:
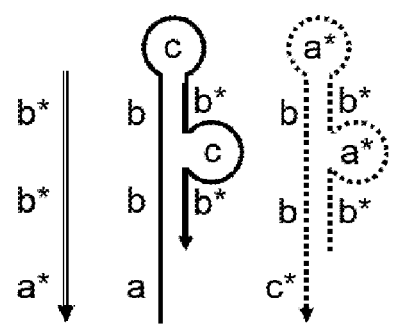
FIG. 7a-7f show schematically a superlinear embodiment of the hybridization chain reaction (HCR).

In FIG. 7a, molecule 1 (the analyte) is a single-strand DNA (ssDNA) target consisting of three sub-sequences in order b*-b*-a* from 5' to 3' on the strand. Molecules 2 and 3 are building blocks for the ultimate product and are hairpin structures, each with two bulged-loops protruding in the middle of the double-strand (dsDNA) region. The sequence of molecule 2 is a-b-b-c-b*-c-b* while that of molecule 3 is b*-a*-b*-a*-b-b-c*. Sub-sequences a, a*, c, and c* are sufficiently short (e.g., approximately 4-8 residues) that when held in their loop structures they are unavailable for hybridization with their sequence complements. Sub-sequences b and b* are sufficiently long (e.g., approximately 9-18 residues) that their dsDNA stem structures are stable and do not allow the protected loops to open up. Molecule 2 is shown as a solid line and molecule 3 as a dotted line for ease in tracking.

Figure 7B:
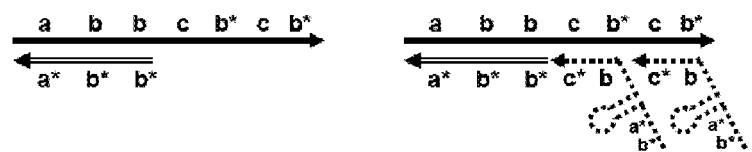
Figure 7C:
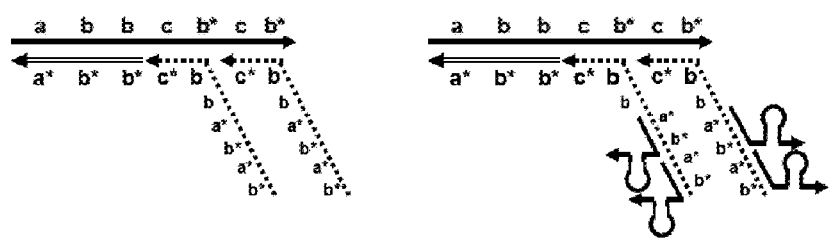

In the first step, molecule 1 hybridizes with molecule 2 at a, and by strand displacement at both b sequences, opens molecule 2, resulting in the complex 4 shown in FIG. 7b.

In complex 4 the c-b*-c-b* ssDNA region is now available for hybridizing to two copies of molecule 3 by binding the free c* on molecule 3 to form the first cascade layer in the new complex 5, also shown in FIG. 7b. The hybridized copies of molecule 3 partially open via strand displacement and match their b sub-sequences with the b* sub-sequences exposed in complex 4. With some tunable probability (as discussed further below), the remaining b*-a*-b stem-loop will open to expose another available copy of a*, as shown in complex 6 in FIG. 7c.

Figure 7D:
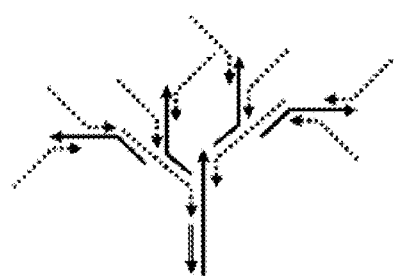

Complex 6 is the same as complex 5 except with the remaining stem-loops on the two copies of molecule 3 open (unhybridized). This transition can be facilitated either by 1) modifying the 5' most sub-sequence b on molecule 3 to a sub-sequence ~b which contains sequence mismatches (e.g., non-complementary base pairs) when annealed with b* and/or by 2) including some ssDNA with sequence b* (or ~b*) in the reaction mixture to hybridize with the b (or ~b) sub-sequence. Complex 6 now has 4 sites b*a* available to hybridize to ab sub-sequences in molecule 2, to obtain complex 7. Complex 7 is formed when four copies of molecule 2 react with complex 6. The process continues by strand displacement, stem-loop openings, and hybridization of eight copies of molecule 3 to form the third order cascade complex as shown in FIG. 7d.

Complex 8 is shown in simplified schematic form without specific sub-sequence labels, but molecules 2 and 3 are drawn as solid lines and dotted lines, respectively. On the leaves of the growing tree-like complex, each of the eight copies of molecule 3 display two copies of b*-a* which are available for hybridization and opening of a total of sixteen copies of molecule 2 for the fourth layer of the cascade complex, and so on. Alternating layers of molecules 3 and 2 will continue binding to grow large, branched supramolecular complexes.

These large complexes are visible as high molecular weight bands following electrophoresis and ethidium bromide staining of the native samples on polyacrylamide gels.

Figure 7E:
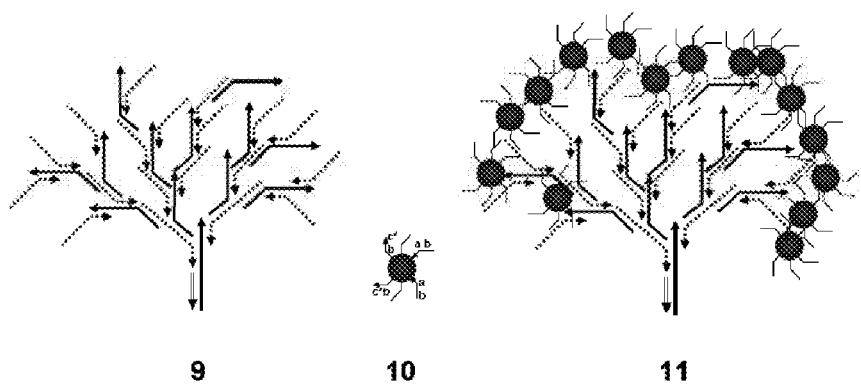
Figure 7F:
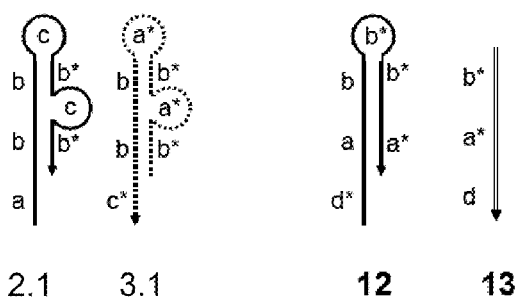

In addition, immediate, naked-eye detection is obtained using DNA-AuNP's as shown in FIG. 7e. Complex 11 shows a AuNP decorated ACR tree complex formed by the addition of DNA-AuNP complex 10 and DNA complex 9. Complex 10 is a conjugate of mixed thiol-labeled DNA strands b-a-C6SS and C6SS-b-c* (where C6SS is the disulfide form and shows the modification site on the oligonucleotide). These DNA labels on the AuNP's hybridize with b*- a* on open 3 molecules and with c-b* on open 2 molecules, thus clustering the AuNP together within range for plasmonic coupling to produce a macroscopic color change from red to blue.

As mentioned above, the sub-sequence b closest to the 3' end on molecule 2 and the sub-sequence b closest to the 5' end on molecule 3 can be replaced with sub-sequence ~b which is similar to b, but contains a small number (e.g., 1-4) of sequence changes which introduce mismatched base-pairings in the ~b/b* double helix. This would serve to slightly destabilize the remaining stem-loop structures shown in complexes 5 and 7 above. This opening reaction needs to be very high yield in order to make the ACR grow exponentially. If this opening is less efficient, the complex will still grow with super-linear scaling, but perhaps less than exponential, thus slight destabilization of the indicated stem might be desirable.

In the illustration above, initial step in which the analyte DNA (1) is able to open, completely, the double-looped molecule 2, requires that the target DNA contain a repeat sequence, in order to effect sufficient strand displacement. Thus, the illustrated target DNA in molecule 1 has the sequence b*b*a*. Such a repeat sequence may not exist in the desired target. However, the NSD can be adapted to accommodate any target nucleotide sequence by using an adaptor illustrated by molecule 12 in FIG. 7f.

Arbitrary analyte sequence d-a*-b* (molecule 13) opens the adaptor molecule 12 to expose a sequence b*-b*-a* which, like their sequence in original analyte molecule 1, initiates the cascade of components 2.1 and 3.1 as described above.

The procedure of this example can also be performed using a nucleic acid aptamer or enzyme capable of allosteric modulation as NSD as described in U.S. 2006/0026178 and U.S. 2006/0035275A1.

Allozyme-based NSD's, can detect a wide range of analytes, from small molecules (including divalent metal ions) to macromolecular structures. In the absence of analyte, the conformation of the NSD sequesters the triggering strand. In the presence of the analyte that binds the allosteric aptamer or enzyme, the NSD undergoes an conformational switch, exposing a triggering strand analogous to molecule 1 above. This analyte-bound open form thus initiates the ACR by exposing the triggering strand.

A. A specific embodiment of this example uses the following sequences:

```
Building block molecule 2:
5'-CCT AAA CCA CGC CGA ATC CAC TCA CGC CGA ATC CAC

TCA AAG TAA GTG GAT TCG GCG TGC AAA GTA AGT GGA

TTC GGC GTG (SEQ ID NO: 39);

Building block molecule 3:
5'-AGT GGA TTC GGC GTG GTT TAG GAG TGG ATT CGG CGT

GGT TTA GGC ACG CCG AAT CCA CTC ACG CCG AAT CCA

CTT ACT TTG (SEQ ID NO: 40);

analyte molecule 1:
5'-AGT GGA TTC GGC GTG AGT GGA TTC GGC GTG GTT TAG

G (SEQ ID NO: 41);

Detection molecule 10 (b-c*):
5'-C6SS-A₁₀-CA CGC CGA ATC CAC TTA CTT TG
(SEQ ID NO: 42); and Detection molecule 10 (a-b):
5'-C6SS-A₁₀-CCT AAA CCA CGC CGA ATC CAC T
(SEQ ID NO: 43).
```

B. The procedure of this example is performed using a 34 nucleotide analyte DNA uniquely identifying the multicopy cryptic plasmid of Chlamydia trachomatis genome as analyte:

```
Analyte DNA 13:
5'-GCA AAT AAT CCT TGG GAC AAA ATC AAC ACC TGT C;
(SEQ ID NO: 44);

NSD 12:
5'-GAC AGG TGT TGA TTT TGT CCC AAG GAT TAT TTG CGC

AAA TAA TCC TTG GGC AAA TAA TCC TTG GGA CAA AA
(SEQ ID NO: 45);

Building block molecule 2.1:
5'-TTT TGT CCC AAG GAT TAT TTG CCC AAG GAT TAT TTG

CCA AAG TAG CAA ATA ATC CTT GGC AAA GTA GCA AAT

AAT CCT TGG (SEQ ID NO: 46);

Building block molecule 3.1:
5'-GCA AAT AAT CCT TGG GAC AAA AGC AAA TAA TCC TTG

GGA CAA AAC CAA GGA TTA TTT GCC CAA GGA TTA TTT

GCT ACT TTG (SEQ ID NO: 47);

Detection molecule Ct (b-c*):
5'-C6SS-AAAAAAAAAA-CCA AGG ATT ATT TG CTA CTT TG
(SEQ ID NO: 48); and Detection molecule Ct (a-b):
5'-C6SS-AAAAAAAAAA-TTT TGT CCC AAG GAT TAT TTG C
(SEQ ID NO: 49).
```

EXAMPLE 3.0

Figure 8:
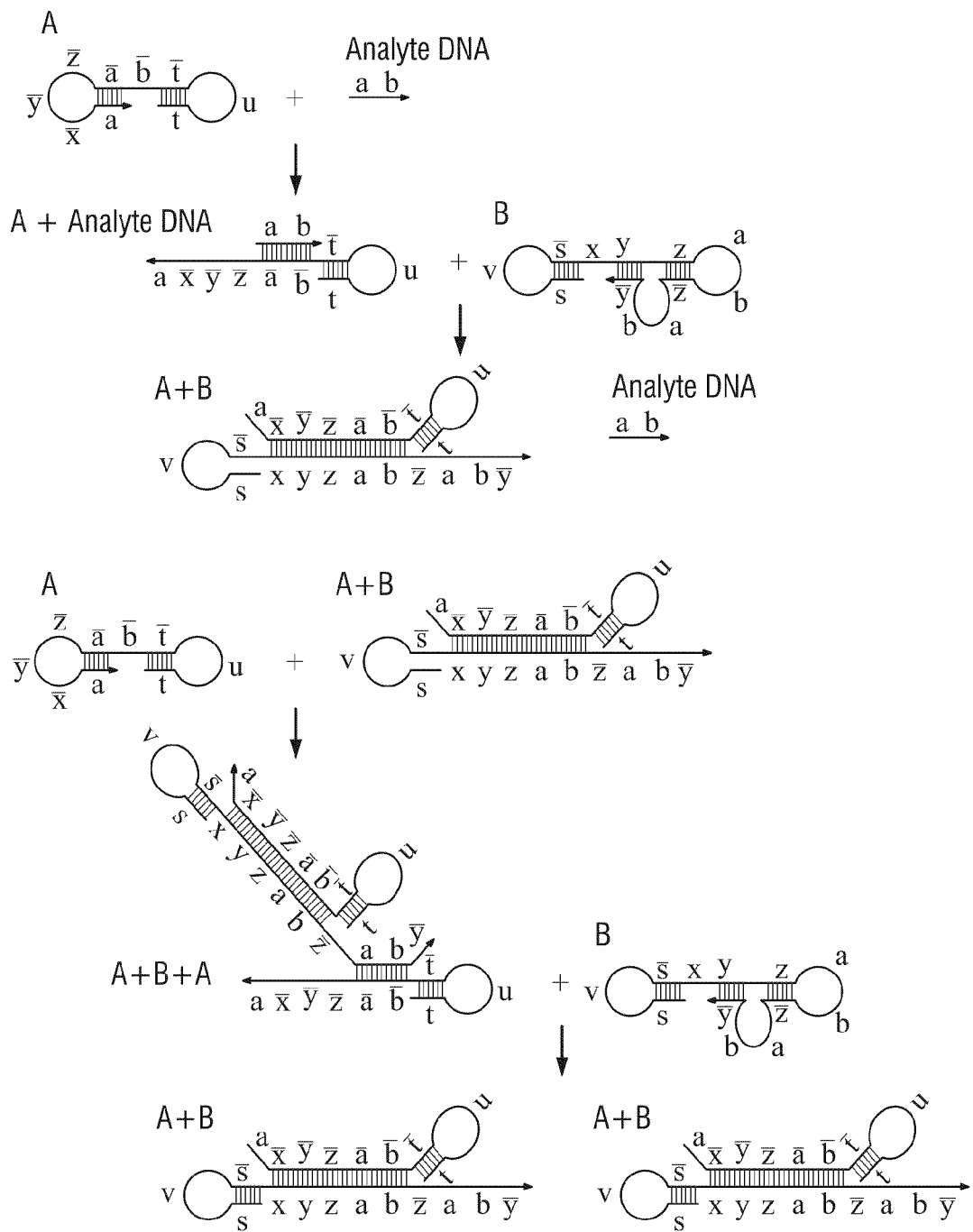
FIG. 8 shows NSD and ACR modules composed of two sequences, A and B.

In the procedure of Example 2.0, the analyte is a short single-stranded DNA hidden within the structure of an allosteric DNA molecule. The analyte, shown in FIG. 8, will affect the status of two independently synthesized DNA nanostructures (A and B in FIG. 8). When A and B are added together without the analyte DNA they remain stable in the closed position. Upon addition of the analyte DNA, a series of hybridizations occurs, opening up a single stranded section of B that contains a copy of the analyte strand (portion a-b). Repetitions of this reaction involving the newly exposed copies of the analyte DNA induces a chain reaction of amplification of copies of the analyte DNA. These copies of the analyte DNA grow exponentially with time, as illustrated in FIG. 8. The method is completely autonomous and requires no thermal cycling.

Figure 9:
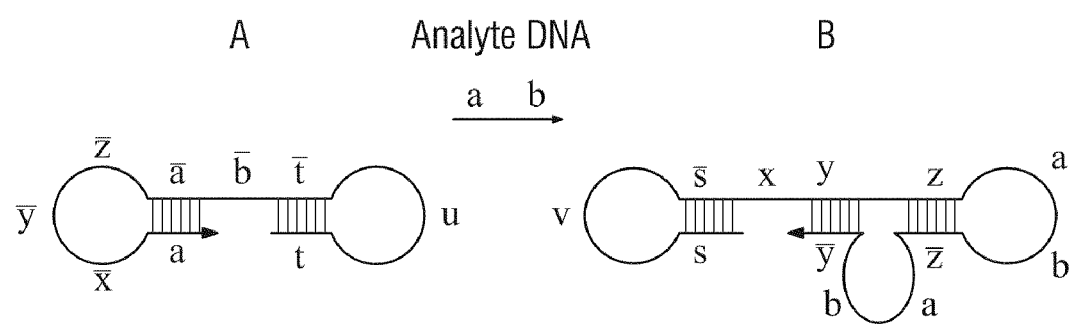
FIG. 9 shows a modified NSD for the procedure of FIG. 8.

In this embodiment, the NSD is modified to decrease the background of false positives. As seen in FIG. 9, the stem structures at the end of A (t and t*) and B (s and s*) are of critical importance. The system detects the presence of analyte DNA and involves two copies of the analyte DNA sequestered inside another component (in this case component B). The presence of such structures coupled with the looped structure in A and B can help to effectively inhibit unwanted hybridization, e.g., that between b* in A and b in B. It is possible for A and B to form dimers/multimers, but these are expected not to affect the intended reactions negatively. Furthermore, we can decrease the probability of forming dimers by decreasing the concentration of the DNA strands. The overall reactions are:

Analyte DNA+$A$=>Analyte DNA·$A$

Analyte DNA·$A$+$B$=>$A$·$B$+Analyte DNA

A·B+A=>A·B·A

A·B·A+B=>2A·B

It is important that A and B are single strands; otherwise, we can not ensure stoichiometry (equimolar) of reactants. Solution A and solution B are kept separate until the method is applied, then equal amounts of A and B combined, along with the analyte DNA.

This procedure of this example is performed using the following sequences:

```
analyte DNA:
5'-CGC TCG CTA GGT TGA AGT CA (SEQ ID NO: 50);

NSD-ACR Sequence A:
5'-atgc AAT GAG GG cataa GCA TCT CTG GCC CTC AtT gcat TGA CTT CAA CCT AGC GAG CGA ACG TGC CAA TTC TGA TCT ACT GTG TGG taaa CGC TCG CTA GGT
(SEQ ID NO: 51;) and NSD-ACR Sequence B:
5'-tccg CGA CGA TT cataa GCA TCT CTG GAA TCG TCG cgg Attta CCA CAC AGT AGA TCA GAA TTG GCA CGT TCG

CTC GCT AGG TTG AAG TCA AAC GTG CCA ATT CGC TCG

CTA GGT TGA AGT CAC TGA TCT ACT GT (SEQ ID NO: 52).
```

EXAMPLE 4.0

Super Linear Kinetics in Rolling Circle Amplification (RCA)

This example illustrates improved forms of rolling circle synthesis and amplification described in U.S. Pat. Nos. 5,854,033 and 5,714,320. A mixture of a single-stranded circular DNA template (which serves the function of an NSD), DNA polymerase, a restriction enzyme, and a short DNA oligonucleotide that comprises one strand of a particular restriction recognition sequence is used to detect an analyte.

Figure 10:
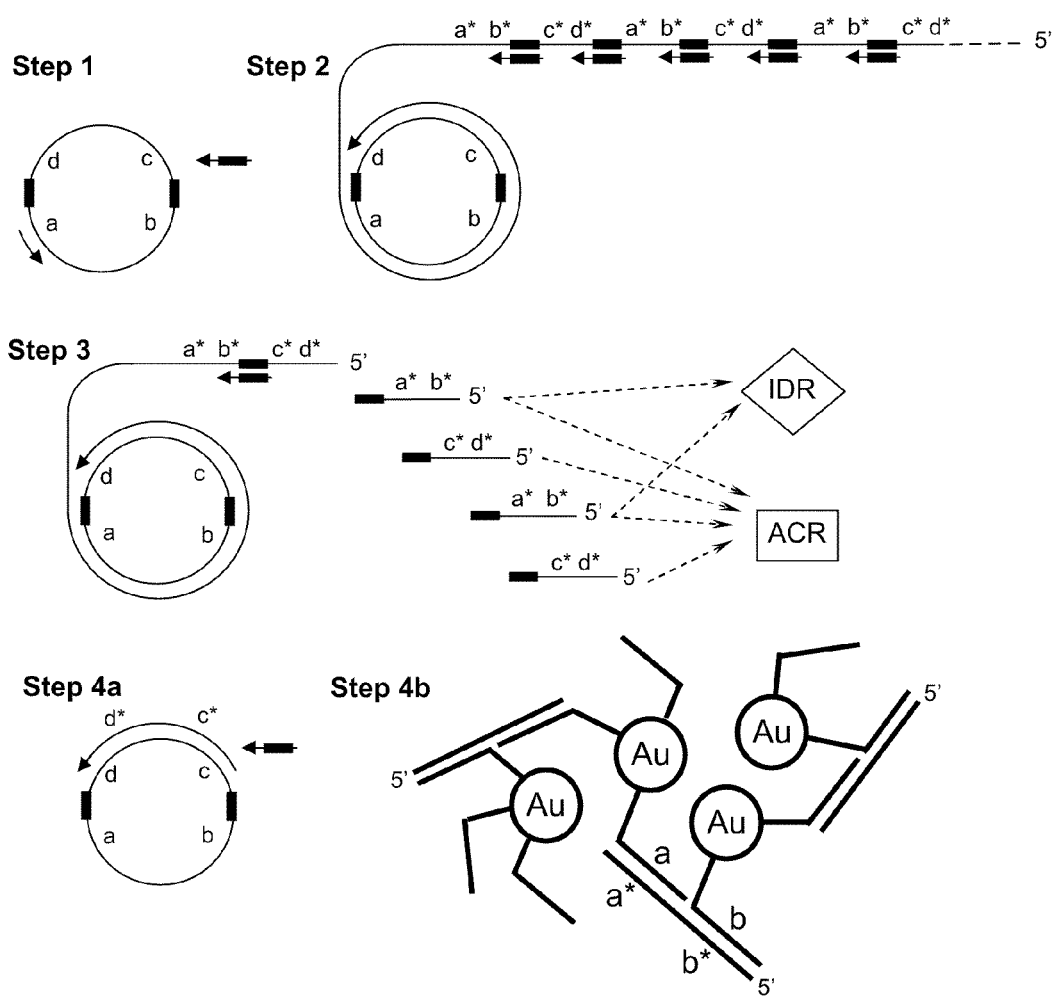
FIG. 10 shows the steps in detection of a DNA analyte using exponential rolling circle amplification (RCA).

The circular DNA template is composed of four distinct sub-sequences having the 5' to 3' arrangement: a, b, c and d, where a and b are separated from c and d by two identical restriction sites (depicted in FIG. 10 by black rectangles). The restriction sites of the circular template are methylated, thus protecting the circular template from enzyme digestion and subsequent linearization. The analyte is a DNA oligonucleotide having a sequence a* complementary to at least a segment of sub-sequence a.

FIG. 10 illustrates the basic operation of this particular embodiment. In Step 1, the circular template, NSD detects the analyte DNA sequence (shown as an arrow in FIG. 10) via sequence specific binding. The bound analyte acts as a primer of the polymerase reaction, triggering the ACR process by primer extension polymerization. In Step 2, after finishing one full circle of extension, the polymerase then displaces the product strand and continues through additional cycles around the circular template, continuously displacing the growing linear strand, creating a linear, single-strand multimer product as in standard RCA. The product strand hybridizes to the oligonucleotides complementary to the restriction sites, creating at these sites, double-stranded regions of DNA susceptible to enzymatic cleavage.

In Step 3, endonuclease digestion yields many independent copies of a*b* and c*d* sequences, both capable of priming additional RCA reactions, Step 4a. Many copies of the a*b* and c*d* sequences are produced from any particular priming event, creating an ACR with super-linear kinetics.

The liberated a*b* sequences provide the basis for the detection (IDR) (Step 4b) by acting as bridging sequences for AuNP's functionalized with either a or b DNA sequences. Hence a dramatic red-blue color change permits the rapid detection of even a single analyte molecule by visual inspection with the naked eye.

A. The procedure described above is performed using a circular template DNA synthesized as a linear single-stranded, 78-mer and enzymatically using CircLigase™ from Epicenter Biotechnologies, and gel purified.

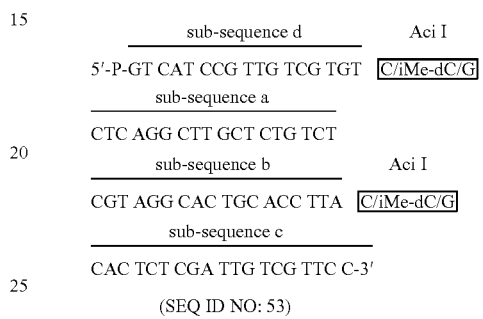

| sub-sequence d | Aci I |
|---|---|
| 5'-P-GT CAT CCG TTG TCG TGT | C/iMe-dC/G |
| sub-sequence a | |
| CTC AGG CTT GCT CTG TCT | |
| sub-sequence b | Aci I |
| CGT AGG CAC TGC ACC TTA | C/iMe-dC/G |
| sub-sequence c | |
| CAC TCT CGA TTG TCG TTC C-3' | |
| (SEQ ID NO: 53) | |

The two restriction sites in the template (boxed sequences) were designed for the endonuclease Aci I, which cuts at 5'-C|CGC-3', but is inhibited when the second C is methylated. Methylation was included in the synthesis procedure. The analyte DNA was 5'-CAG AGC AAG CCT GA (SEQ ID NO:54). The sequence of the 4-mer oligonucleotides complementary for restriction digest was 5'-GCGG.

The circularized template was mixed with the polymerase, Φ29, an enzyme capable of strand-displacement and more than 70,000 nucleotide extensions per priming event. Using PAGE and ethidium bromide staining as the IDR, the analyte DNA was detected in quantities less than 30 nM.

B. The procedure described in paragraph A of this example was followed, but replacing the PAGE IDR with the DNA-AuNP colorimetric method described herein. Four distinct sequences, analogs of the a, b, c, and d sequences from the circular template, were synthesized for AuNP functionalization:

```
a, 5'-C6SS-A10-AGA CAG AGC AAG CCT GAG
   (SEQ ID NO: 55);

b, 5'-C6SS-A10-CGG TAA GGT GCA GTG CCT ACG
   (SEQ ID NO: 56);

c, 5'-C6SS-A10-GGA ACG ACA ATC GAG AGT G
   (SEQ ID NO: 57); and d, 5'-C6SS-A10-CGG ACA GCA CAA CGG ATG AC
   (SEQ ID NO: 58).
```

Each a*b* product can thus bridge the a and b derivatized Au, and each c*d* product bridges the c and d derivatized Au to obtain networks of gold nanoparticles.

C. The procedure described in paragraph B of this example is followed, where the a and b sub-sequences of the circular template (as well as the analogous a and b sequences that functionalize the AuNP's) were modified to hybridize to a 20 nucleotide analyte sequence uniquely identifying the Human Immunodeficiency Virus (HIV), Cao, Y. C., et al., *Science* (2002) 297:1536.

The sequences are:

```
Circular Template:
5'-P-GT CAT CCG TTG TCG TGT C/iMe-dC/G C AGA AGA

TAT TTG GAA TAA CAT GAC CTG GAT GCA C/iMe-dC/G C

AC TCT CGA TTG TCG TTC C (SEQ ID NO: 59);

analyte DNA:
5'-TAT TCC AAA TAT CTT CT (SEQ ID NO: 60);
and

C6SS capped DNA for AuNP functionalization:
5'-C6SS-A₁₀-TAT TCC AAA TAT CTT CTG (SEQ ID NO: 61),
and

5'-C6SS-A₁₀-CGG TGC ATC CAG GTC AGT T
(SEQ ID NO: 62).
```

D. The procedure of paragraph B of this example is followed where the a and b sub-sequences of the circular template (as well as the analogous a and b sequences that functionalize the AuNP's) were modified to hybridize to the 21 nucleotide analyte sequence uniquely identifying *Chlamydia trachomatis* (Little, M. C., et al., *Clinical Chemistry* (1999) supra)).

The sequences are:

```
Circular Template:
5'-P-GT CAT CCG TTG TCG TGT C/iMe-dC/GC GGA TAG

AGT AGT GGT CAT CTC GTT GGG CTC ATA AC/iMe-dC/G

CAC TCT CGA TTG TCG TTC C (SEQ ID NO: 63);

analyte DNA:
5'-GAT GAC CAC TAC TCT ATC C (SEQ ID NO: 64);

C6SS capped DNA for AuNP functionalization:
5'-C6SS-A₁₀-GAT GAC CAC TAC TCT ATC CG
(SEQ ID NO: 65), and

5'-C6SS-A₁₀-CGG TTA TGA GCC CAA CGA
(SEQ ID NO: 66).
```

EXAMPLE 5.0

Displacement of Multiple FRET Detectors

Figure 11:
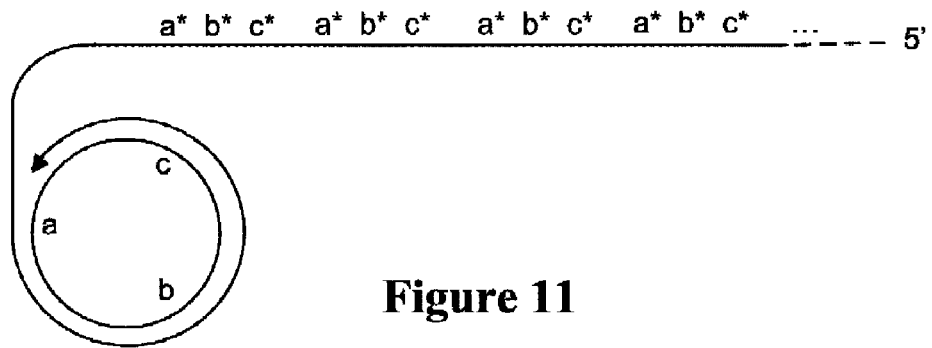
FIG. 11 shows how RCA is used to synthesize long, single stranded multiple repeats of the complement of the circular template sub-sequences a, b, and c. The sequence complements contained in the circular template are denoted by *. The single stranded products, comprised of 100's or 1,000's of repeats, are subsequently gel purified.
Figure 12:
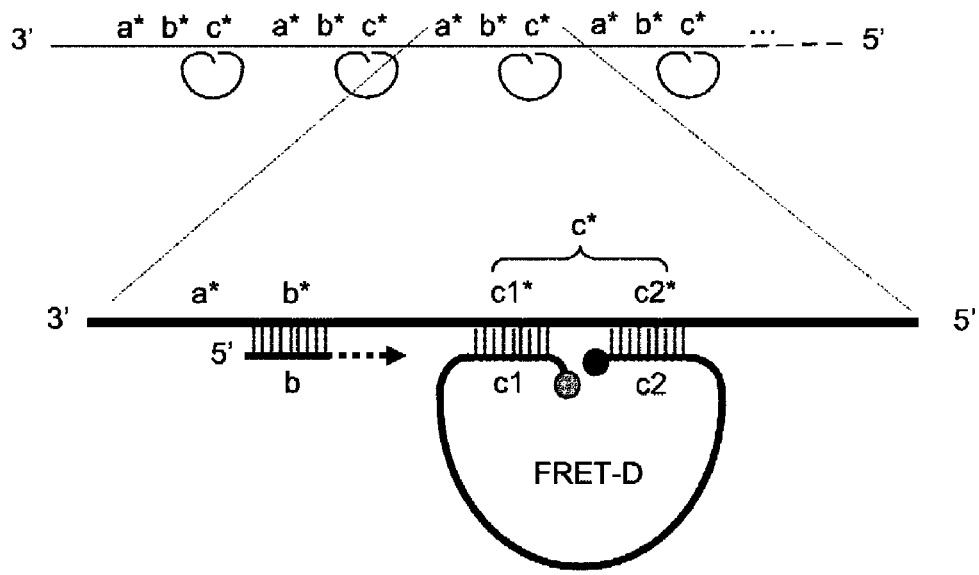
FIG. 12 shows the details of single stranded RCA products of FIG. 11. The analyte DNA (b), binds to the b*, priming DNA polymerization (dotted arrow). When hybridized, the FRET quencher and fluorophore groups on FRET-D are proximal, thus quenching fluorescence.

Hybridization of a nucleic acid analyte to a long template strand hybridized to multiple repeating FRET detectors primes extension catalyzed by a processive polymerase. This displaces the multiple FRET detectors generating a fluorescent signal. To prepare the assay system, RCA is conveniently used to synthesize long, linear, single-stranded DNA's, that are multiple repeats of the complement of the circular template. The template is comprised of three sub-sequences arranged in the 5' to 3' order: the RCA primer-binding sequence a; the analyte-binding sequence b, the FRET detector binding sequence c, as shown in FIG. 11. Sequences a and b in this example are distinct but could, in principle, be the same. Sub-sequence c is comprised of two sub-sequences, (c1) and (c2), complementary to sub-sequences found on the FRET detector sequence (FIG. 12). The linear products of the RCA are gel purified from the circular templates.

The purified linear products are then loaded with the FRET detector sequence (FRET-D) shown in FIG. 12. The FRET-D sequence has sub-sequence c1 near its 3' end, and sub-sequence c2 at its 5' terminal, permitting base-pairing to the RCA product as shown. Located terminally on FRET-D are quencher and fluorophore groups. In the bound state, with the 5' and 3' ends in proximity, fluorescence is inactivated. This configuration of RCA product and bound FRET-D comprise a poised fluorescence detector for a DNA analyte having sequence b.

Figure 13:
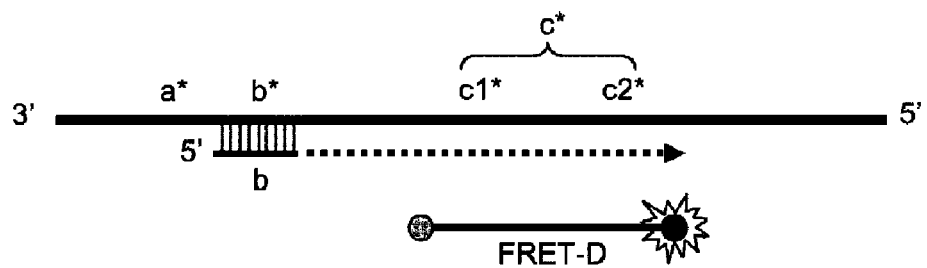
FIG. 13 shows how DNA polymerase displaces the FRET-D sequence of FIG. 12, activating fluorescence.

The DNA analyte binds to b* of the RCA product, priming DNA polymerase, which begins synthesizing a complementary DNA strand 5' to 3', as shown in FIG. 13. The DNA polymerase displaces the bound FRET-D sequence allowing the quencher and fluorophore groups to diffuse and create a fluorescent signal. Although many polymerases could operate on a single FRET-D-loaded RCA product, processive DNA polymerases (such as Φ29) will displace many FRET-D sequences from a single priming event. Hence, even low molar quantities of the DNA analyte will generate substantial fluorescent signal.

The invention claimed is:

1. A method to determine the presence or absence of an analyte in a sample which method comprises
contacting said sample with
a nanometer scale switching device (NSD) comprised of a nucleic acid that is specific for, and activated by, the presence of the analyte such that the NSD will remain in its off state in the absence of the analyte and switch to its on state in the presence of the analyte,
components comprised of nucleic acids that are components of an autocatalytic chain reaction (ACR) process which process is initiated by activation of the NSD or directly by the analyte, and operates with superlinear kinetics to produce a product wherein each subsequent ACR reaction cycle produces more than one further product from each product previously formed with a rate of product growth increasing over time, and an indicator (IDR) responsive to said product; and detecting the presence or absence of any response of the IDR to said product as indicative of the presence or absence of the analyte, wherein said ACR comprises an autocatalytic nucleic acid cleavage reaction, wherein said autocatalytic nucleic acid reaction opens a covalently circularized ribozyme or deoxyribozyme achieving a linearized form.

2. The method of claim 1, wherein the analyte effects an allosteric transformation in said NSD to release or expose a trigger that initiates the ACR.

3. The method of claim 2, wherein the NSD is activated by a substance other than a nucleic acid or by a photon, an α particle or a β particle.

4. The method of claim 1, wherein said autocatalytic nucleic acid cleavage reaction opens a covalently circularized inactive form of a ribozyme or deoxyribozyme achieving a linearized active form of said ribozyme or deoxyribozyme, and wherein the NSD comprises a second inactive form of said ribozyme or deoxyribozyme that is activated in the presence of analyte, and wherein the product is the linearized active ribozymes or deoxyribozymes, and wherein all components are dissolved in solution phase and not attached to a solid support.

5. The method of claim 4, wherein said analyte activates an intermediate that activates said second inactive form of said ribozyme or deoxyribozyme.

6. The method of claim 4, wherein the ribozyme or deoxyribozyme is the 10-23 deoxyribozyme.

7. The method of claim 4, wherein said IDR employs colorimetric detection wherein DNA labeled gold nanoparticles (DNA-AuNP) are added to the reaction after an appropriate time period such that the ACR proceeds sufficiently such that the DNA-AuNP do not halt the ACR prematurely.

8. A composition for performing the method of claim 1, which composition comprises covalently circularized inactive ribozymes or deoxyribozymes which are activated by linearization via backbone bond cleavage, wherein a linearized active form of said ribozymes or deoxyribozymes recognizes and opens said covalently circularized inactive ribozymes or deoxyribozymes in an ACR process that is characterized by superlinear kinetics, produces a product and is initiated by an activated NSD or by an analyte, an IDR responsive to said product, and optionally comprising an NSD specific for, and activated by, said analyte.

9. A kit for performance of the method of claim 1 containing, optionally in separate containers, covalently circularized inactive ribozymes or deoxyribozymes which are activated by linearization via backbone bond cleavage, wherein a linearized active form of said ribozymes or deoxyribozymes recognizes and opens said covalently circularized inactive ribozymes or deoxyribozymes in an ACR process that is characterized by superlinear kinetics that produces a linearized product with a rate of product growth increasing over time and is initiated by an activated NSD or by an analyte, an IDR responsive to said product, and optionally an NSD specific for, and activated by, said analyte.

* * * * *

SEQUENCE LISTING

```
<160> NUMBER OF SEQ ID NOS: 66

<210> SEQ ID NO 1
<211> LENGTH: 54
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(54)
<223> OTHER INFORMATION: L1D sequence

<400> SEQUENCE: 1
tttatccgtc cctcctagtg tttttcacta ggaggctagc tacaacgagg gacg      54

<210> SEQ ID NO 2
<211> LENGTH: 21
<212> TYPE: DNA
<213> ORGANISM: Artificial Sequence
<220> FEATURE:
<223> OTHER INFORMATION: Synthetic construct
<220> FEATURE:
```

```
<221> NAME/KEY: misc_feature
<222> LOCATION: (1)...(21)
<223> OTHER INFORMATION: analyte DNA

<400> SEQUENCE: 2
ccactaggag ggacggataa a                                              21

<210> SEQ ID NO 3
<211> LENGTH: 31
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(31)
<223> OTHER INFORMATION: linear C2 sequence
<220> FEATURE:
<221> NAME/KEY: misc_feature
<222> LOCATION: 1
<223> OTHER INFORMATION: adenosine has phosphate group at 5' position
<220> FEATURE:
<221> NAME/KEY: misc_RNA
<222> LOCATION: (18)...(19)
<223> OTHER INFORMATION: RNA linkage to uracil

<400> SEQUENCE: 3
agctacaacg acgtcccauc ctagtgaggc t                                   31

<210> SEQ ID NO 4
<211> LENGTH: 31
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(31)
<223> OTHER INFORMATION: linear C1 sequence
<220> FEATURE:
<221> NAME/KEY: misc_feature
<222> LOCATION: 1
<223> OTHER INFORMATION: adenosine has phosphate group at 5' position
<220> FEATURE:
<221> NAME/KEY: misc_RNA
<222> LOCATION: (18)...(19)
<223> OTHER INFORMATION: RNA linkage to uracil

<400> SEQUENCE: 4
agctacaacg agggacgauc actaggaggc t                                   31

<210> SEQ ID NO 5
<211> LENGTH: 26
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(26)
<223> OTHER INFORMATION: synthetic DNA oligomer
<220> FEATURE:
<221> NAME/KEY: misc_feature
<222> LOCATION: (17)...(26)
<223> OTHER INFORMATION: poly-adenine sub-sequence
<220> FEATURE:
<221> NAME/KEY: misc_feature
<222> LOCATION: 26
<223> OTHER INFORMATION: C6SS 6-carbon-alkane-disulfide group cap

<400> SEQUENCE: 5
gctagcctca ctaggaaaaa aaaaaa                                         26
```

```
<210> SEQ ID NO 6
<211> LENGTH: 25
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(25)
<223> OTHER INFORMATION: synthetic DNA oligomer
<220> FEATURE:
<221> NAME/KEY: misc_feature
<222> LOCATION: (1)...(10)
<223> OTHER INFORMATION: poly-adenine sub-sequence
<220> FEATURE:
<221> NAME/KEY: misc_feature
<222> LOCATION: 1
<223> OTHER INFORMATION: C6SS 6-carbon-alkane-disulfide group cap

<400> SEQUENCE: 6
aaaaaaaaaa tgggacgtcg ttgta                                          25

<210> SEQ ID NO 7
<211> LENGTH: 57
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(57)
<223> OTHER INFORMATION: L1D sequence

<400> SEQUENCE: 7
ccgacctttg ggttatgagc ccatttttgg gctcaggcta gctacaacga taaccca       57

<210> SEQ ID NO 8
<211> LENGTH: 23
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(23)
<223> OTHER INFORMATION: analyte DNA

<400> SEQUENCE: 8
tgggctcata acccaaaggt cgg                                            23

<210> SEQ ID NO 9
<211> LENGTH: 31
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(31)
<223> OTHER INFORMATION: linear C2 sequence
<220> FEATURE:
<221> NAME/KEY: misc_feature
<222> LOCATION: 1
<223> OTHER INFORMATION: adenosine has phosphate group at 5' position
<220> FEATURE:
<221> NAME/KEY: misc_RNA
<222> LOCATION: (19)...(20)
<223> OTHER INFORMATION: RNA linkage to uracil

<400> SEQUENCE: 9
agctacaacg atgggttaau gagcccaggc t                                   31
```

```
<210> SEQ ID NO 10
<211> LENGTH: 31
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(31)
<223> OTHER INFORMATION: linear C1 sequence
<220> FEATURE:
<221> NAME/KEY: misc_feature
<222> LOCATION: 1
<223> OTHER INFORMATION: adenosine has phosphate group at 5' position
<220> FEATURE:
<221> NAME/KEY: misc_RNA
<222> LOCATION: (19)...(20)
<223> OTHER INFORMATION: RNA linkage to uracil

<400> SEQUENCE: 10
agctacaacg ataacccaau gggctcaggc t                              31

<210> SEQ ID NO 11
<211> LENGTH: 25
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(25)
<223> OTHER INFORMATION: synthetic DNA oligomer
<220> FEATURE:
<221> NAME/KEY: misc_feature
<222> LOCATION: (16)...(25)
<223> OTHER INFORMATION: poly-adenine sub-sequence
<220> FEATURE:
<221> NAME/KEY: misc_feature
<222> LOCATION: 25
<223> OTHER INFORMATION: C6SS 6-carbon-alkane-disulfide group cap

<400> SEQUENCE: 11
gctagcctgg gctcaaaaaa aaaaa                                     25

<210> SEQ ID NO 12
<211> LENGTH: 26
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(26)
<223> OTHER INFORMATION: synthetic DNA oligomer
<220> FEATURE:
<221> NAME/KEY: misc_feature
<222> LOCATION: 1
<223> OTHER INFORMATION: C6SS 6-carbon-alkane-disulfide group cap
<220> FEATURE:
<221> NAME/KEY: misc_feature
<222> LOCATION: (1)...(10)
<223> OTHER INFORMATION: poly-adenine sub-sequence

<400> SEQUENCE: 12
aaaaaaaaaa ttaacccatc gttgta                                    26

<210> SEQ ID NO 13
<211> LENGTH: 56
<212> TYPE: DNA
<213> ORGANISM: Artificial Sequence
<220> FEATURE:
<223> OTHER INFORMATION: Synthetic construct
<220> FEATURE:
```

```
<221> NAME/KEY: misc_feature
<222> LOCATION: (1)...(56)
<223> OTHER INFORMATION: L1D sequence

<400> SEQUENCE: 13
gtcatgttat tccaaatatc ttcttttgaa gataggctag ctacaacgat ttggaa          56

<210> SEQ ID NO 14
<211> LENGTH: 23
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(23)
<223> OTHER INFORMATION: analyte DNA

<400> SEQUENCE: 14
gaagatattt ggaataacat gac                                              23

<210> SEQ ID NO 15
<211> LENGTH: 31
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(31)
<223> OTHER INFORMATION: linear C2 sequence
<220> FEATURE:
<221> NAME/KEY: misc_feature
<222> LOCATION: 1
<223> OTHER INFORMATION: adenosine has phosphate group at 5' position
<220> FEATURE:
<221> NAME/KEY: misc_RNA
<222> LOCATION: (19)...(20)
<223> OTHER INFORMATION: RNA linkage to uracil

<400> SEQUENCE: 15
agctacaacg attccaaaau atcttcaggc t                                     31

<210> SEQ ID NO 16
<211> LENGTH: 32
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(31)
<223> OTHER INFORMATION: linear C1 sequence
<220> FEATURE:
<221> NAME/KEY: misc_feature
<222> LOCATION: 1
<223> OTHER INFORMATION: adenosine has phosphate group at 5' position
<220> FEATURE:
<221> NAME/KEY: misc_RNA
<222> LOCATION: (19)...(20)
<223> OTHER INFORMATION: RNA linkage to uracil

<400> SEQUENCE: 16
agctacaacg atttggaara ugaagatagg ct                                    32

<210> SEQ ID NO 17
<211> LENGTH: 25
<212> TYPE: DNA
<213> ORGANISM: Artificial Sequence
<220> FEATURE:
<223> OTHER INFORMATION: Synthetic construct
<220> FEATURE:
```

```
<221> NAME/KEY: misc_feature
<222> LOCATION: (1)...(25)
<223> OTHER INFORMATION: synthetic DNA oligomer
<220> FEATURE:
<221> NAME/KEY: misc_feature
<222> LOCATION: (16)...(25)
<223> OTHER INFORMATION: poly-adenine sub-sequence
<220> FEATURE:
<221> NAME/KEY: misc_feature
<222> LOCATION: 25
<223> OTHER INFORMATION: C6SS 6-carbon-alkane-disulfide group cap

<400> SEQUENCE: 17
gctagcctga agataaaaaa aaaaa                                         25

<210> SEQ ID NO 18
<211> LENGTH: 26
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(26)
<223> OTHER INFORMATION: synthetic DNA oligomer
<220> FEATURE:
<221> NAME/KEY: misc_feature
<222> LOCATION: 1
<223> OTHER INFORMATION: C6SS 6-carbon-alkane-disulfide group cap
<220> FEATURE:
<221> NAME/KEY: misc_feature
<222> LOCATION: (1)...(10)
<223> OTHER INFORMATION: poly-adenine sub-sequence

<400> SEQUENCE: 18
aaaaaaaaaa ttttggaatc gttgta                                        26

<210> SEQ ID NO 19
<211> LENGTH: 97
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(97)
<223> OTHER INFORMATION: L1D sequence

<400> SEQUENCE: 19
gccaggactc ttgcctggag ctgcttaatg ccccagaccg tgagttttta ctcacggtct   60
ggggcaggct agctacaacg attaagcagc tccaggc                            97

<210> SEQ ID NO 20
<211> LENGTH: 45
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(45)
<223> OTHER INFORMATION: analyte DNA

<400> SEQUENCE: 20
actcacggtc tggggcatta agcagctcca ggcaagagtc ctggc                   45

<210> SEQ ID NO 21
<211> LENGTH: 33
<212> TYPE: DNA
<213> ORGANISM: Artificial Sequence
<220> FEATURE:
```

```
<223> OTHER INFORMATION: Synthetic construct
<220> FEATURE:
<221> NAME/KEY: misc_feature
<222> LOCATION: (1)...(33)
<223> OTHER INFORMATION: linear C2 sequence
<220> FEATURE:
<221> NAME/KEY: misc_feature
<222> LOCATION: 1
<223> OTHER INFORMATION: adenosine has phosphate group at 5' position
<220> FEATURE:
<221> NAME/KEY: misc_RNA
<222> LOCATION: (20)...(21)
<223> OTHER INFORMATION: RNA linkage to uracil

<400> SEQUENCE: 21
agctacaacg actgcttaaa ugccccagag gct                                    33

<210> SEQ ID NO 22
<211> LENGTH: 33
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(33)
<223> OTHER INFORMATION: linear C1 sequence
<220> FEATURE:
<221> NAME/KEY: misc_feature
<222> LOCATION: 1
<223> OTHER INFORMATION: adenosine has phosphate group at 5' position
<220> FEATURE:
<221> NAME/KEY: misc_RNA
<222> LOCATION: (20)...(21)
<223> OTHER INFORMATION: RNA linkage to uracil

<400> SEQUENCE: 22
agctacaacg attaagcaga uctgggcag gct                                     33

<210> SEQ ID NO 23
<211> LENGTH: 26
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(26)
<223> OTHER INFORMATION: synthetic DNA oligomer
<220> FEATURE:
<221> NAME/KEY: misc_feature
<222> LOCATION: (17)...(26)
<223> OTHER INFORMATION: poly-adenine sub-sequence
<220> FEATURE:
<221> NAME/KEY: misc_feature
<222> LOCATION: 26
<223> OTHER INFORMATION: C6SS 6-carbon-alkane-disulfide group cap

<400> SEQUENCE: 23
gctagcctgc cccagaaaaa aaaaaa                                            26

<210> SEQ ID NO 24
<211> LENGTH: 27
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(27)
<223> OTHER INFORMATION: synthetic DNA oligomer
<220> FEATURE:
<221> NAME/KEY: misc_feature
<222> LOCATION: (1)...(10)
```

```
<223> OTHER INFORMATION: poly-adenine sub-sequence
<220> FEATURE:
<221> NAME/KEY: misc_feature
<222> LOCATION: 1
<223> OTHER INFORMATION: C6SS 6-carbon-alkane-disulfide group cap

<400> SEQUENCE: 24
aaaaaaaaaa tctgcttaat cgttgta                                              27

<210> SEQ ID NO 25
<211> LENGTH: 26
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(26)
<223> OTHER INFORMATION: synthetic DNA oligomer
<220> FEATURE:
<221> NAME/KEY: misc_feature
<222> LOCATION: (17)...(26)
<223> OTHER INFORMATION: poly-adenine sub-sequence
<220> FEATURE:
<221> NAME/KEY: misc_feature
<222> LOCATION: 26
<223> OTHER INFORMATION: C6SS 6-carbon-alkane-disulfide group cap

<400> SEQUENCE: 25
gctagcctct ggggcaaaaa aaaaaa                                               26

<210> SEQ ID NO 26
<211> LENGTH: 27
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(27)
<223> OTHER INFORMATION: synthetic DNA oligomer
<220> FEATURE:
<221> NAME/KEY: misc_feature
<222> LOCATION: (1)...(10)
<223> OTHER INFORMATION: poly-adenine sub-sequence
<220> FEATURE:
<221> NAME/KEY: misc_feature
<222> LOCATION: 1
<223> OTHER INFORMATION: C6SS 6-carbon-alkane-disulfide group cap

<400> SEQUENCE: 26
aaaaaaaaaa tttaagcagt cgtggta                                              27

<210> SEQ ID NO 27
<211> LENGTH: 91
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(91)
<223> OTHER INFORMATION: L1D sequence

<400> SEQUENCE: 27
ggattcggac ctccgacctt tgggttatga gcccaacgag atttttatct cgttgggctc          60
aggctagcta caacgataac ccaaaggtcg g                                         91

<210> SEQ ID NO 28
<211> LENGTH: 42
<212> TYPE: DNA
```

<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(42)
<223> OTHER INFORMATION: analyte DNA

<400> SEQUENCE: 28
atctcgttgg gctcataacc caaaggtcgg aggtccgaat cc                          42

<210> SEQ ID NO 29
<211> LENGTH: 90
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(90)
<223> OTHER INFORMATION: L1D sequence

<400> SEQUENCE: 29
atccaggtca tgttattcca aatatttatc cgtccctcct agtggtcact aggaggctag       60
ctacaacgag ggacgtattt ggaataacat                                        90

<210> SEQ ID NO 30
<211> LENGTH: 24
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(24)
<223> OTHER INFORMATION: analyte DNA

<400> SEQUENCE: 30
tatttggaat aacatgacct ggat                                              24

<210> SEQ ID NO 31
<211> LENGTH: 31
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(32)
<223> OTHER INFORMATION: linear C2 sequence
<220> FEATURE:
<221> NAME/KEY: misc_feature
<222> LOCATION: 1
<223> OTHER INFORMATION: adenosine has phosphate group at 5' position
<220> FEATURE:
<221> NAME/KEY: misc_RNA
<222> LOCATION: (18)...(19)
<223> OTHER INFORMATION: RNA linkage to uracil

<400> SEQUENCE: 31
agctacaacg acgtcccauc ctagtgaggc t                                      31

<210> SEQ ID NO 32
<211> LENGTH: 31
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(31)

```
<223> OTHER INFORMATION: linear C1 sequence
<220> FEATURE:
<221> NAME/KEY: misc_feature
<222> LOCATION: 1
<223> OTHER INFORMATION: adenosine has phosphate group at 5' position
<220> FEATURE:
<221> NAME/KEY: misc_RNA
<222> LOCATION: (18)...(19)
<223> OTHER INFORMATION: RNA linkage to uracil

<400> SEQUENCE: 32
agctacaacg agggacgauc actaggaggc t                              31

<210> SEQ ID NO 33
<211> LENGTH: 40
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(40)
<223> OTHER INFORMATION: analyte DNA from cryptic plasmid of Chlamydia
      trachomatis genome

<400> SEQUENCE: 33
caacacctgt cgcagccaaa atgacagctt ctgatggaat                     40

<210> SEQ ID NO 34
<211> LENGTH: 85
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(85)
<223> OTHER INFORMATION: Nanoswitch detector

<400> SEQUENCE: 34
attccatcag aagctgtcat tttggctgcg acaggtgttg cactaggagg gacggataaa    60
caacacctgt cgcagccaaa atgac                                         85

<210> SEQ ID NO 35
<211> LENGTH: 53
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(53)
<223> OTHER INFORMATION: L1D sequence

<400> SEQUENCE: 35
tttatccgtc cctcctagtg ttttcactag gaggctagct acaacgaggg acg         53

<210> SEQ ID NO 36
<211> LENGTH: 41
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(41)
<223> OTHER INFORMATION: analyte DNA from cryptic plasmid of Chlamydia
      trachomatis genome

<400> SEQUENCE: 36
```

```
gtcgcagcca aaatgacagc ttctgatgga atatctttaa c                    41
```

<210> SEQ ID NO 37
<211> LENGTH: 86
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(86)
<223> OTHER INFORMATION: DNA analyte detector

<400> SEQUENCE: 37

```
gttaaagata ttccatcaga agctgtcatt ttggtgcgac cactaggagg gacggataaa    60
gtcgcagcca aaatgacagc ttctga                                         86
```

<210> SEQ ID NO 38
<211> LENGTH: 70
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(70)
<223> OTHER INFORMATION: DNA analyte detector

<400> SEQUENCE: 38

```
ttccatcaga agctgtcatt ttggctgcga ccactaggag ggacggataa agtcgcagcc    60
aaaatgacag                                                           70
```

<210> SEQ ID NO 39
<211> LENGTH: 81
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(81)
<223> OTHER INFORMATION: Building block molecule 2

<400> SEQUENCE: 39

```
cctaaaccac gccgaatcca ctcacgccga atccactcaa agtaagtgga ttcggcgtgc    60
aaagtaagtg gattcggcgt g                                              81
```

<210> SEQ ID NO 40
<211> LENGTH: 81
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(81)
<223> OTHER INFORMATION: Building block molecule 3

<400> SEQUENCE: 40

```
agtggattcg gcgtggttta ggagtggatt cggcgtggtt taggcacgcc gaatccactc    60
acgccgaatc cacttacttt g                                              81
```

<210> SEQ ID NO 41
<211> LENGTH: 37
<212> TYPE: DNA
<213> ORGANISM: Artificial Sequence
<220> FEATURE:

```
<223> OTHER INFORMATION: Synthetic construct
<220> FEATURE:
<221> NAME/KEY: misc_feature
<222> LOCATION: (1)...(37)
<223> OTHER INFORMATION: Analyte molecule 1

<400> SEQUENCE: 41
agtggattcg gcgtgagtgg attcggcgtg gtttagg                              37

<210> SEQ ID NO 42
<211> LENGTH: 32
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(32)
<223> OTHER INFORMATION: Detection molecule 10 (b-c*)
<220> FEATURE:
<221> NAME/KEY: misc_feature
<222> LOCATION: 1
<223> OTHER INFORMATION: C6SS 6-carbon-alkane-disulfide group cap
<220> FEATURE:
<221> NAME/KEY: misc_feature
<222> LOCATION: (1)...(10)
<223> OTHER INFORMATION: poly-adenine sub-sequence

<400> SEQUENCE: 42
aaaaaaaaaa cacgccgaat ccacttactt tg                                  32

<210> SEQ ID NO 43
<211> LENGTH: 32
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(32)
<223> OTHER INFORMATION: Detection molecule 10 (a-b)
<220> FEATURE:
<221> NAME/KEY: misc_feature
<222> LOCATION: 1
<223> OTHER INFORMATION: C6SS 6-carbon-alkane-disulfide group cap
<220> FEATURE:
<221> NAME/KEY: misc_feature
<222> LOCATION: (1)...(10)
<223> OTHER INFORMATION: poly-adenine sub-sequence

<400> SEQUENCE: 43
aaaaaaaaaa cctaaaccac gccgaatcca ct                                  32

<210> SEQ ID NO 44
<211> LENGTH: 34
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(34)
<223> OTHER INFORMATION: Analyte DNA 13

<400> SEQUENCE: 44
gcaaataatc cttgggacaa aatcaacacc tgtc                                34

<210> SEQ ID NO 45
<211> LENGTH: 71
<212> TYPE: DNA
<213> ORGANISM: Artificial Sequence
<220> FEATURE:
```

<223> OTHER INFORMATION: Synthetic construct
<220> FEATURE:
<221> NAME/KEY: misc_feature
<222> LOCATION: (1)...(71)
<223> OTHER INFORMATION: Nanoswitch detector 12

<400> SEQUENCE: 45
gacaggtgtt gattttgtcc caaggattat ttgcgcaaat aatccttggg caaataatcc    60
ttgggacaaa a    71

<210> SEQ ID NO 46
<211> LENGTH: 81
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(81)
<223> OTHER INFORMATION: Building block molecule 2.1

<400> SEQUENCE: 46
ttttgtccca aggattattt gcccaaggat tatttgccaa agtagcaaat aatccttggc    60
aaagtagcaa ataatccttg g    81

<210> SEQ ID NO 47
<211> LENGTH: 81
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(81)
<223> OTHER INFORMATION: Building block molecule 3.1

<400> SEQUENCE: 47
gcaaataatc cttgggacaa aagcaaataa tccttgggac aaaaccaagg attatttgcc    60
caaggattat ttgctacttt g    81

<210> SEQ ID NO 48
<211> LENGTH: 32
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(32)
<223> OTHER INFORMATION: Detection molecule Ct (b-c*)
<220> FEATURE:
<221> NAME/KEY: misc_feature
<222> LOCATION: 1
<223> OTHER INFORMATION: C6SS 6-carbon-alkane-disulfide group cap
<220> FEATURE:
<221> NAME/KEY: misc_feature
<222> LOCATION: (1)...(10)
<223> OTHER INFORMATION: poly-adenine sub-sequence

<400> SEQUENCE: 48
aaaaaaaaaa ccaaggatta tttgctactt tg    32

<210> SEQ ID NO 49
<211> LENGTH: 32
<212> TYPE: DNA
<213> ORGANISM: Artificial Sequence
<220> FEATURE:
<223> OTHER INFORMATION: Synthetic construct
<220> FEATURE:

```
<221> NAME/KEY: misc_feature
<222> LOCATION: (1)...(32)
<223> OTHER INFORMATION: Detection molecule Ct (a-b)
<220> FEATURE:
<221> NAME/KEY: misc_feature
<222> LOCATION: 1
<223> OTHER INFORMATION: C6SS 6-carbon-alkane-disulfide group cap
<220> FEATURE:
<221> NAME/KEY: misc_feature
<222> LOCATION: (1)...(10)
<223> OTHER INFORMATION: poly-adenine sub-sequence

<400> SEQUENCE: 49
aaaaaaaaaa ttttgtccca aggattattt gc                                   32

<210> SEQ ID NO 50
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(20)
<223> OTHER INFORMATION: Analyte DNA

<400> SEQUENCE: 50
cgctcgctag gttgaagtca                                                 20

<210> SEQ ID NO 51
<211> LENGTH: 103
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(103)
<223> OTHER INFORMATION: Nanoswitch detector-autocatalytic chain
      reaction sequence A

<400> SEQUENCE: 51
atgcaatgag ggcataagca tctctggccc tcattgcatt gacttcaacc tagcgagcga     60
acgtgccaat tctgatctac tgtgtggtaa acgctcgcta ggt                      103

<210> SEQ ID NO 52
<211> LENGTH: 135
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(135)
<223> OTHER INFORMATION: Nanoswitch detector-autocatalytic chain
      reaction sequence B

<400> SEQUENCE: 52
tccgcgacga ttcataagca tctctggaat cgtcgcggat ttaccacaca gtagatcaga     60
attggcacgt tcgctcgcta ggttgaagtc aaacgtgcca attcgctcgc taggttgaag    120
tcactgatct actgt                                                    135

<210> SEQ ID NO 53
<211> LENGTH: 78
<212> TYPE: DNA
<213> ORGANISM: Artificial Sequence
<220> FEATURE:
<223> OTHER INFORMATION: Synthetic construct
<220> FEATURE:
```

<221> NAME/KEY: misc_feature
<222> LOCATION: (1)...(78)
<223> OTHER INFORMATION: circular template DNA synthesized as linear
      single stranded mer
<220> FEATURE:
<221> NAME/KEY: misc_feature
<222> LOCATION: 1
<223> OTHER INFORMATION: guanine has phosphate group at 5' position
<220> FEATURE:
<221> NAME/KEY: misc_feature
<222> LOCATION: 19, 57
<223> OTHER INFORMATION: methylated cytosine

<400> SEQUENCE: 53
gtcatccgtt gtcgtgtccg ctcaggcttg ctctgtctcg taggcactgc accttaccgc    60
actctcgatt gtcgttcc                                                  78

<210> SEQ ID NO 54
<211> LENGTH: 14
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(14)
<223> OTHER INFORMATION: Analyte DNA

<400> SEQUENCE: 54
cagagcaagc ctga                                                      14

<210> SEQ ID NO 55
<211> LENGTH: 28
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(27)
<223> OTHER INFORMATION: analog of A sequence from DNA circular template
<220> FEATURE:
<221> NAME/KEY: misc_feature
<222> LOCATION: 1
<223> OTHER INFORMATION: C6SS 6-carbon-alkane-disulfide group cap
<220> FEATURE:
<221> NAME/KEY: misc_feature
<222> LOCATION: (1)...(10)
<223> OTHER INFORMATION: poly-adenine sub-sequence

<400> SEQUENCE: 55
aaaaaaaaaa agacagagca agcctgag                                       28

<210> SEQ ID NO 56
<211> LENGTH: 31
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(31)
<223> OTHER INFORMATION: analog of B sequence from DNA circular template
<220> FEATURE:
<221> NAME/KEY: misc_feature
<222> LOCATION: 1
<223> OTHER INFORMATION: C6SS 6-carbon-alkane-disulfide group cap
<220> FEATURE:
<221> NAME/KEY: misc_feature
<222> LOCATION: (1)...(10)
<223> OTHER INFORMATION: poly-adenine sub-sequence

<400> SEQUENCE: 56
aaaaaaaaaa cggtaaggtg cagtgcctac g                                    31

<210> SEQ ID NO 57
<211> LENGTH: 29
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(29)
<223> OTHER INFORMATION: analog of sequence C from DNA circular template
<220> FEATURE:
<221> NAME/KEY: misc_feature
<222> LOCATION: 1
<223> OTHER INFORMATION: C6SS 6-carbon-alkane-disulfide group cap
<220> FEATURE:
<221> NAME/KEY: misc_feature
<222> LOCATION: (1)...(10)
<223> OTHER INFORMATION: poly-adenine sub-sequence

<400> SEQUENCE: 57
aaaaaaaaaa ggaacgacaa tcgagagtg                                       29

<210> SEQ ID NO 58
<211> LENGTH: 30
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(30)
<223> OTHER INFORMATION: analog of sequence D from DNA circular template
<220> FEATURE:
<221> NAME/KEY: misc_feature
<222> LOCATION: 1
<223> OTHER INFORMATION: C6SS 6-carbon-alkane-disulfide group cap
<220> FEATURE:
<221> NAME/KEY: misc_feature
<222> LOCATION: (1)...(10)
<223> OTHER INFORMATION: poly-adenine sub-sequence

<400> SEQUENCE: 58
aaaaaaaaaa cggacagcac aacggatgac                                      30

<210> SEQ ID NO 59
<211> LENGTH: 76
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(76)
<223> OTHER INFORMATION: DNA circular template
<220> FEATURE:
<221> NAME/KEY: misc_feature
<222> LOCATION: 1
<223> OTHER INFORMATION: guanine has phosphate group at 5" position
<220> FEATURE:
<221> NAME/KEY: misc_feature
<222> LOCATION: 19, 56
<223> OTHER INFORMATION: methylated cytosine

<400> SEQUENCE: 59
gtcatccgtt gtcgtgtccg cagaagatat ttggaataac atgacctgga tgcaccgcac     60
tctcgattgt cgttcc                                                     76

<210> SEQ ID NO 60
<211> LENGTH: 17

```
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(17)
<223> OTHER INFORMATION: Analyte DNA

<400> SEQUENCE: 60
tattccaaat atcttct                                                    17

<210> SEQ ID NO 61
<211> LENGTH: 28
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(28)
<223> OTHER INFORMATION: synthetic DNA oligomer
<220> FEATURE:
<221> NAME/KEY: misc_feature
<222> LOCATION: 1
<223> OTHER INFORMATION: C6SS 6-carbon-alkane-disulfide group cap
<220> FEATURE:
<221> NAME/KEY: misc_feature
<222> LOCATION: (1)...(10)
<223> OTHER INFORMATION: poly-adenine sub-sequence

<400> SEQUENCE: 61
aaaaaaaaaa tattccaaat atcttctg                                        28

<210> SEQ ID NO 62
<211> LENGTH: 29
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(29)
<223> OTHER INFORMATION: synthetic DNA oligomer
<220> FEATURE:
<221> NAME/KEY: misc_feature
<222> LOCATION: 1
<223> OTHER INFORMATION: C6SS 6-carbon-alkane-disulfide group cap
<220> FEATURE:
<221> NAME/KEY: misc_feature
<222> LOCATION: (1)...(10)
<223> OTHER INFORMATION: poly-adenine sub-sequence

<400> SEQUENCE: 62
aaaaaaaaaa cggtgcatcc aggtcagtt                                       29

<210> SEQ ID NO 63
<211> LENGTH: 77
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(77)
<223> OTHER INFORMATION: DNA circular template
<220> FEATURE:
<221> NAME/KEY: misc_feature
<222> LOCATION: 1
<223> OTHER INFORMATION: guanine has phosphate group at 5' position
<220> FEATURE:
<221> NAME/KEY: misc_feature
<222> LOCATION: 19, 57
<223> OTHER INFORMATION: methylated cytosine
```

```
<400> SEQUENCE: 63
gtcatccgtt gtcgtgtccg cggatagagt agtggtcatc tcgttgggct cataaccgca        60
ctctcgattg tcgttcc                                                      77

<210> SEQ ID NO 64
<211> LENGTH: 19
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(19)
<223> OTHER INFORMATION: analyte DNA

<400> SEQUENCE: 64
gatgaccact actctatcc                                                    19

<210> SEQ ID NO 65
<211> LENGTH: 30
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(30)
<223> OTHER INFORMATION: synthetic DNA oligomer
<220> FEATURE:
<221> NAME/KEY: misc_feature
<222> LOCATION: 1
<223> OTHER INFORMATION: C6SS 6-carbon-alkane-disulfide group cap
<220> FEATURE:
<221> NAME/KEY: misc_feature
<222> LOCATION: (1)...(10)
<223> OTHER INFORMATION: poly-adenine sub-sequence

<400> SEQUENCE: 65
aaaaaaaaaa gatgaccact actctatccg                                        30

<210> SEQ ID NO 66
<211> LENGTH: 28
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(28)
<223> OTHER INFORMATION: synthetic DNA oligomer
<220> FEATURE:
<221> NAME/KEY: misc_feature
<222> LOCATION: 1
<223> OTHER INFORMATION: C6SS 6-carbon-alkane-disulfide group cap
<220> FEATURE:
<221> NAME/KEY: misc_feature
<222> LOCATION: (1)...(10)
<223> OTHER INFORMATION: poly-adenine sub-sequence

<400> SEQUENCE: 66
aaaaaaaaaa cggttatgag cccaacga                                          28
```